US012781304B2

(12) United States Patent
Fukushima

(10) Patent No.: US 12,781,304 B2
(45) Date of Patent: Nov. 3, 2026

(54) METAL RECOVERY MATERIAL, AND METHOD FOR RECOVERING METAL FROM SOLUTION INCLUDING METAL ION OR METAL COMPLEX ION

(71) Applicant: IHI Corporation, Tokyo (JP)

(72) Inventor: Yasuyuki Fukushima, Tokyo (JP)

(73) Assignee: IHI Corporation, Tokyo (JP)

( * ) Notice: Subject to any disclaimer, the term of this patent is extended or adjusted under 35 U.S.C. 154(b) by 455 days.

(21) Appl. No.: 18/685,955

(22) PCT Filed: Aug. 25, 2022

(86) PCT No.: PCT/JP2022/032088
§ 371 (c)(1),
(2) Date: Feb. 23, 2024

(87) PCT Pub. No.: WO2023/032815
PCT Pub. Date: Mar. 9, 2023

(65) Prior Publication Data
US 2024/0384368 A1 Nov. 21, 2024

(30) Foreign Application Priority Data
Aug. 31, 2021 (JP) ................................ 2021-141684

(51) Int. Cl.
*C22B 3/18* (2006.01)
*B01D 15/00* (2006.01)
*B01J 20/24* (2006.01)
*C12N 1/125* (2026.01)
*C12N 1/205* (2026.01)
*C22B 11/00* (2006.01)

(52) U.S. Cl.
CPC ................ *C22B 3/18* (2013.01); *B01D 15/00* (2013.01); *B01J 20/24* (2013.01); *C12N 1/125* (2021.05); *C12N 1/205* (2021.05); *C22B 11/04* (2013.01); *B01J 2220/4831* (2013.01)

(58) Field of Classification Search
CPC ........... C22B 3/18; C22B 11/04; C12N 1/205; C12N 1/125; B01D 15/00; B01J 20/24; B01J 2220/4831
USPC .......................................................... 423/23
See application file for complete search history.

(56) References Cited

U.S. PATENT DOCUMENTS

2019/0024209 A1 1/2019 Minoda
2020/0002782 A1 1/2020 Minoda et al.

FOREIGN PATENT DOCUMENTS

| | | | |
|---|---|---|---|
| CA | 2 721 235 | C | 3/2016 |
| JP | 2013-056290 | A | 3/2013 |
| JP | 2013-067826 | A | 4/2013 |
| JP | 2017-061739 | A | 3/2017 |
| JP | 6826996 | B2 | 2/2021 |
| WO | 2009/130006 | A1 | 10/2009 |
| WO | 2013/042340 | A1 | 3/2013 |
| WO | 2017/111092 | A1 | 6/2017 |
| WO | 2018155687 | A1 | 8/2018 |

OTHER PUBLICATIONS

Darley, W. Marshall, "Algal Biology: a physiological approach", Baifukan Co., Ltd, 1987, p. 184.

(Continued)

*Primary Examiner* — Anita Nassiri-Motlagh

(57) ABSTRACT

A metal recovery material contains a blue-green alga of the genus *Leptolyngbya.*

19 Claims, 16 Drawing Sheets

(56) References Cited

OTHER PUBLICATIONS

Kinya Atsumi, "Purpose of Algal Research and Its Status of Development", Denso Technical Review, 2017, vol. 22, p. 181-p. 186.
"Metal recycling", DOWA Eco-System Co., Ltd., https://www.dowa-eco.co.jp/business/recycle/metal_recycle/, retrieved on Dec. 27, 2023.
"Fiscal 2012 report on study of feasibility of collecting rare metals in and the like in Seawater", The Engineering Advancement Association of Japan, Mar. 2013.
Toyohisa Fujita et al., "Adsorption of Metal Ions by River Algae", Journal of MMIJ, 1992, vol. 108, No. 2, p. 123-p. 128.
Benjamin Greene et al., "Interaction of Gold(I) and Gold(III) Complexes with Algal Biomass", Environ. Sci. Technol., 1986, vol. 20, No. 6, p. 627-p. 632.
Masashi Hojo, "Why Can Pure Gold Be Dissolved in Seawater Mixed with Aqueous Nitric Acid?", Bunseki Kagaku, 2014, vol. 63, No. 9, p. 715-p. 726.
Masashi Hojo et al., "Can pure gold be dissolved in seawater mixed with aqueous nitric acid?", Journal of Molecular Liquids, 2014, vol. 194, p. 68-p. 76.
Xiaohui Ju et al., "Effective and selective recovery of gold and palladium ions from metal wastewater using a sulfothermophilic red alga, *Galdieria sulphuraria*", Bioresource Technology, 2016, vol. 211, p. 759-p. 764.
Masatoshi Kondo et al., "Recovery of Lithium from Seawater", J. Plasma Fusion Res., 2011, vol. 87, No. 12, p. 795-p. 800.
Nural Kuyucak et al., "Recovery of gold by a new biosorbent", Precious Metals 1986, Proceedings of the Tenth International Precious Metals Institute Conference, International Precious Metals Institute, 1986, p. 211-p. 216.
Saeko Nomura, "Trivia on foreign object inspection", Food Analysis Technology Center Sunatec, http://www.mac.or.jp/mail/120801/03.shtml, 2012.
Tatsuo Nozaki et al., "Rapid growth of mineral deposits at artificial seafloor hydrothermal vents", Scientific Reports, 2016, vol. 6, p. 1-p. 10.
Dipannita Parial et al., "Screening of different algae for green synthesis of gold nanoparticles", Eur. J. Phycol., 2012, vol. 47, No. 1, p. 22-p. 29.
P. Dheeban Shankar et al., "A review on the biosynthesis of metallic nanoparticles (gold and silver) using bio-components of microalgae: Formation mechanism and applications", Enzyme and Microbial Technology, 2016, vol. 95, p. 28-p. 44.
"Implementation status of the small home appliance recycling system", https://www.meti.go.jp/shingikai/sankoshin/sangyo_gijutsu/haikibutsu_recycle/kogata_wg/pdf/001_02_00.pdf, 2015.
Lu Xing et al., "Global Gold Nanoparticles Market Research Report 2018", QYResearch, Dec. 2018.
Shin'ya Yamamoto, "Biofuel press residue collecting gold", CLICCCAR, https://clicccar.com/2013/10/05/232304/, Oct. 5, 2013.
Tetsuo Yamauchi, "DOWA advances with 'urban mine'", Toyo Keizai Inc., https://shikiho.jp/news/0/22632, Apr. 22, 2010.
Shoei Mizuhashi et al., "Recovery of Precious Metals from Plating Solutions and their Derivatives—On-site Precious Metals Recovery System—", J. Surf. Finish. Soc. Jpn., 2015, vol. 66, No. 3, p. 81-p. 85.
Kohmei Halada, "Possibility and Challenge of Urban Mining", J. Surf. Finish. Soc. Jpn., 2012, vol. 63, No. 10, p. 606-p. 611.

(A)

(B)

(A)

(B)

(A)

(B)

METAL RECOVERY MATERIAL, AND METHOD FOR RECOVERING METAL FROM SOLUTION INCLUDING METAL ION OR METAL COMPLEX ION

CROSS REFERENCE TO RELATED APPLICATIONS

This patent application is a U.S. national stage application under 35 U.S.C. § 371 of International Patent Application No. PCT/JP2022/032088 filed on Aug. 25, 2022, which claims the benefit of foreign priority to Japanese Patent Application No. JP 2021-141684 filed on Aug. 31, 2021. The International Application was published in Japanese on Mar. 9, 2023, as International Publication No. WO 2023/032815 A1 under PCT Article 21 (2).

TECHNICAL FIELD

The present disclosure relates to a metal recovery material and a method for recovering a metal from a solution containing a metal ion or metal complex ion.

BACKGROUND ART

With the economic development of emerging countries, there are concerns about depletion of metal resources, and there is a need for a technique for recovering metal resources from places other than natural mines such as from urban mine and seawater. There are several methods of recovering a metal from a solution in which the metal is dissolved, and among them, a method using algae is more environmentally friendly than a chemical method, and algae is highly promising in that they can be easily cultured in large quantities. As a method using algae, for example, a method which involves adsorbing metal ions in a metal solution to algae (for example, Patent Literature 1) is known.

CITATION LIST

Patent Literature

Patent Literature 1: PCT International Publication No. WO 2018/155687

SUMMARY OF INVENTION

Technical Problem

However, conventional methods of recovering a metal using algae have problems such as cost and yield, and have not been put into practical use. Here, the present disclosure describes a new method for recovering a metal using algae.

Solution to Problem

A metal recovery material according to one aspect of the present disclosure contains a blue-green alga of the genus *Leptolyngbya*.

Effects of Invention

According to the present disclosure, there is provided a new method for recovering a metal using algae.

DESCRIPTION OF EMBODIMENTS

Figure 1:
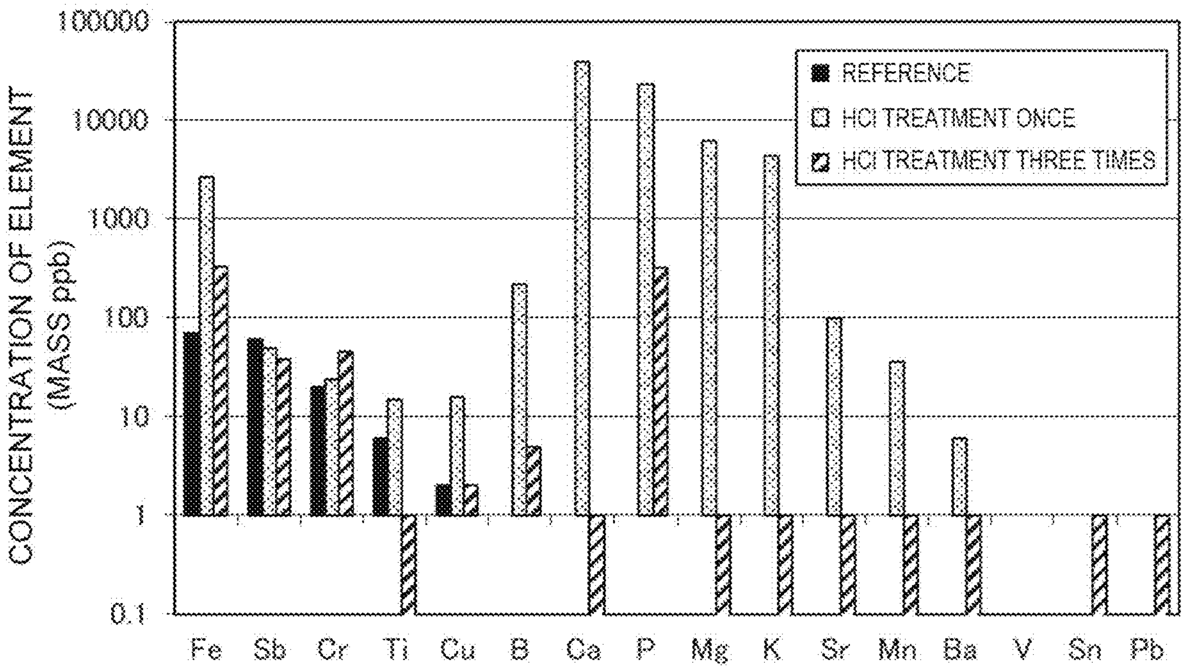
FIG. 1 shows elements contained in a hydrochloric acid waste solution produced when a blue-green alga was treated with hydrochloric acid.

A metal recovery material according to one aspect of the present disclosure contains a blue-green alga of the genus *Leptolyngbya*. The blue-green alga of the genus *Leptolyngbya* may be a blue-green alga of the genus *Leptolyngbya* deposited with accession number FERM BP-22385 (original deposit date: Jan. 17, 2020, depositary authority: The National Institute of Technology and Evaluation, International Patent Organism Depositary (IPOD) (#120, 2-5-8 Kazusakamatari, Kisarazu-shi, Chiba 292-0818, Japan)). The blue-green alga of the genus *Leptolyngbya* may be a dried product of the blue-green alga of the genus *Leptolyngbya*.

A method for recovering a metal from a solution containing a metal ion or metal complex ion according to one aspect of the present disclosure includes a step of immersing a blue-green alga in a solution containing a metal ion or metal complex ion to produce a metal, and the blue-green alga is a blue-green alga of the genus *Leptolyngbya*. The blue-green alga may be a blue-green alga of the genus *Leptolyngbya* deposited with accession number FERM BP-22385 (original deposit date: Jan. 17, 2020, depositary authority: The National Institute of Technology and Evaluation, International Patent Organism Depositary (IPOD) (#120, 2-5-8 Kazusakamatari, Kisarazu-shi, Chiba 292-0818, Japan)).

The blue-green alga is preferably a blue-green alga treated with an acid, and more preferably a blue-green alga further treated with an organic solvent. By using the blue-green alga treated with an acid or treated with an acid and an organic solvent, the amount of metal to be adsorbed to the blue-green alga can be increased. In addition, by using the blue-green alga treated with an acid and an organic solvent, the amount of metal recovered can be improved and the purity of the metal to be recovered can be improved.

The solution containing a metal ion or metal complex ion may be a solution containing an ion or complex ion of at least one metal selected from the group consisting of gold, palladium, platinum, and rhodium, and the metal to be recovered may be at least one selected from the group consisting of gold, palladium, platinum, and rhodium.

The step of immersing a blue-green alga in the solution containing a metal ion or metal complex ion may be performed at 50° C. or higher. By performing the step of immersing a blue-green alga at 50° C. or higher, it is possible to reduce the release of the metal nanoparticles from the blue-green alga and increase the amount of metal nanoparticles adsorbed to the blue-green alga.

In the step of immersing a blue-green alga in the solution containing a metal ion or metal complex ion, the blue-green alga may be immersed while irradiating the solution containing a metal ion or metal complex ion with a visible light or ultraviolet light. Alternatively, in the step of immersing a blue-green alga in the solution containing a metal ion or metal complex ion, the blue-green alga may be immersed while blocking the solution containing a metal ion or metal complex ion from light. By irradiating the solution containing a metal ion or metal complex ion with a visible light or ultraviolet light, particularly a blue light (435 to 490 nm) or ultraviolet light, it is possible to reduce the release of the metal nanoparticles from the blue-green alga and increase the amount of metal nanoparticles adsorbed to the blue-green alga. On the other hand, by blocking the solution containing a metal ion or metal complex ion from light, the amount of metal nanoparticles released from the blue-green alga into the solution can be increased.

The method for recovering a metal from a solution containing a metal ion or metal complex ion according to the present aspect of the present disclosure may further include recovering the metal. The step of recovering the metal may include filtering the solution in which the blue-green alga has been immersed. By filtering the solution in which the blue-green alga has been immersed, the blue-green alga can be separated from the solution in which the blue-green alga has been immersed, and a filtrate containing metal nanoparticles, namely, a metal colloidal solution can be obtained. The step of recovering the metal may include a step of ultrasonicating the blue-green alga. By ultrasonicating the blue-green alga, the metal nanoparticles adsorbed to the blue-green alga can be easily desorbed from the blue-green alga. The step of recovering the metal may include a step of firing the blue-green alga. By firing the blue-green alga, the blue-green alga itself is removed, and the metal adsorbed to the blue-green alga can be recovered.

The solution containing a metal ion or metal complex ion may be a solution obtained by bringing a metal element-containing substance into contact with a dissolving solution containing nitric acid and a salt to dissolve the metal element-containing substance.

The solution containing a metal ion or metal complex ion may be a solution obtained by a method including steps of: bringing the metal element-containing substance into contact with a dissolving solution containing 10 mass % or more of aqua regia to obtain a solution of the metal element-containing substance; and diluting the solution of the metal element-containing substance such that the concentration of aqua regia becomes 5 mass % or less to obtain the solution containing a metal ion or metal complex ion.

The step of immersing a blue-green alga in the solution containing a metal ion or metal complex ion may be a step of (i) immersing the blue-green alga in the solution containing a metal ion or metal complex ion to produce the metal and to adsorb the metal onto the blue-green alga. The method for recovering a metal from a solution containing a metal ion or metal complex ion according to the present aspect of the present disclosure may further include steps of: (ii) recovering the blue-green alga to which the metal has been adsorbed; and (iii) recovering the metal from the recovered blue-green alga. The step (i) of immersing the blue-green alga in the solution containing a metal ion or metal complex ion and the step (ii) of recovering the blue-green alga to which the metal has been adsorbed may be performed twice or more, and the blue-green algae used for the second and subsequent immersions are blue-green algae different from the blue-green alga recovered from the solution containing a metal ion or metal complex ion.

A method for producing gold nanoparticles according to one aspect of the present disclosure includes a step of immersing a blue-green alga in a solution containing a gold ion or gold complex ion to produce gold nanoparticles, and the blue-green alga is a blue-green alga of the genus *Leptolyngbya*.

A method for producing a metal molded product according to one aspect of the present disclosure includes steps of: immersing a blue-green alga in a solution containing a metal ion or metal complex ion to produce a metal and to adsorb the metal onto the blue-green alga; recovering the blue-green alga to which the metal has been adsorbed; molding the recovered blue-green alga; and firing the molded blue-green alga to obtain a metal molded product, and the blue-green alga is a blue-green alga of the genus *Leptolyngbya*.

The metal molded product may be for personal ornaments.

A method for recovering a metal from a solution containing a metal ion or metal complex ion according to one aspect of the present disclosure includes a step of bringing a blue-green alga extract solution into contact with a solution containing a metal ion or metal complex ion to produce a metal, and the blue-green alga is a blue-green alga of the genus *Leptolyngbya*.

Hereinafter, embodiments of the present disclosure will be described in detail.

A metal recovery material according to one aspect of the present disclosure contains a blue-green alga of the genus *Leptolyngbya* (hereinafter simply referred to as "blue-green alga" in some cases). A metal recovery material refers to a material for recovering a metal ion or metal complex ion as a solid metal (including in the form of a metal colloidal solution) from a solution containing the metal ion or metal complex ion. The blue-green alga of the genus *Leptolyngbya* has an ability to reduce the metal ion or metal complex ion in the solution containing the metal ion or metal complex ion to produce a metal atom. For example, when the solution containing a metal ion or metal complex ion contains a tetrachloroaurate (III) ion ($[AuCl_4]^-$), the blue-green alga has an ability to reduce [AuCla] to an Au atom. The produced metal atom is adsorbed to the blue-green alga, and some metal atoms crystallize to form nanoparticles if the amount of adsorption is sufficient. Examples of metal atoms that crystallize to form nanoparticles on the blue-green alga include gold, palladium, platinum, and rhodium. The nanoparticulated metal remains adsorbed to the blue-green alga or is released from the blue-green alga into the solution. Therefore, by immersing the metal recovery material containing a blue-green alga of the genus *Leptolyngbya* in the solution containing a metal ion or metal complex ion, the metal ion or metal complex ion in the solution can be recovered as a solid metal. In addition, metals that can take the form of metal nanoparticles can be recovered as a metal colloidal solution.

The blue-green alga of the genus *Leptolyngbya* may be, for example, a blue-green alga of the genus *Leptolyngbya* deposited to The National Institute of Technology and Evaluation, International Patent Organism Depositary (IPOD) (#120, 2-5-8 Kazusakamatari, Kisarazu-shi, Chiba 292-0818, Japan) with accession number FERM BP-22385 (original deposit date: Jan. 17, 2020).

The blue-green alga is preferably a dried product of the blue-green alga of the genus *Leptolyngbya* from the perspective of storage or preservation (that is, prevention of decay). From the perspective of improving dispersibility in the solution containing a metal ion or metal complex ion, the dried product is preferably in the form of powder.

From the perspective of lowering the S/V ratio (ratio of area to volume) of the dried product of the blue-green alga in order to decrease the weight loss of the dried product of the blue-green alga when the solution containing a metal ion or metal complex ion is an acidic solution, and from the perspective of ease of handling and effective use of space, the dried product of the blue-green alga is more preferably in the form of a sheet (seaweed shape).

From the perspective of increasing the amount of metal to be adsorbed to the blue-green alga, the blue-green alga is preferably a blue-green alga treated with an acid and more preferably a blue-green alga treated with an acid and an organic solvent. The blue-green alga treated with an acid and an organic solvent is preferable also from the perspective of improving the amount of metal recovered and from the perspective of improving purity of the metal to be recovered. Here, treating the blue-green alga with an acid or an organic solvent specifically means immersing the blue-green alga, preferably a blue-green alga washed with water, in an acid or an organic solvent. It should be noted that it is not essential to treat the blue-green alga with an acid and an organic solvent, and the blue-green alga may be treated with neither the acid nor the organic solvent, or the blue-green alga may be treated with only either one of the acid and the organic solvent.

The acid is not particularly limited, and may be, for example, hydrochloric acid, nitric acid, sulfuric acid, or any combination thereof. By treating the blue-green alga with an acid, metal elements (Fe, Cu, B, Ca, P, Mg, K, Sr, Mn, Ba, etc.) constituting the blue-green alga can be removed from the blue-green alga.

From the perspective of increasing the amount of metal to be adsorbed to the blue-green alga, it is preferable that the treatment with an acid is performed once or twice. Treating with an acid twice means immersing the blue-green alga in an acid, removing the acid, and then immersing the blue-green alga in an acid again. The time for acid treatment (that is, the time for immersion in an acid) is not particularly limited, and may be, for example, 5 minutes to 120 minutes, and is desirably 10 minutes to 60 minutes.

The concentration of the acid used in the acid treatment may be, for example, 1 to 15 mass %, and is desirably 5 to 10 mass %. The ratio of the blue-green alga and the acid may be, for example, 1 to 10,000 mL, 10 to 1,000 mL, or 100 to 400 mL of acid with respect to 1 g of blue-green alga.

The organic solvent is not particularly limited, and for example, solvents that can extract photosynthetic pigments such as ethanol, acetone, and dichloromethane may be used. The time for treatment with an organic solvent (that is, the time for immersion in an organic solvent) is preferably 30 minutes to 120 minutes, and more preferably 30 minutes to 60 minutes. The treatment with an organic solvent may be performed before or after treatment with an acid, but is preferably performed after treatment with an acid.

The concentration of the organic solvent may be, for example, 10 to 100 mass % or 50 to 100 mass %, and is desirably 100 mass %. The ratio of the blue-green alga and the organic solvent may be, for example, 0.1 to 10,000 mL, 1 to 1,000 mL, or 10 to 100 mL of organic solvent with respect to 1 g of blue-green alga.

The metal ion, metal complex ion, and a metal to be produced and recovered from these ions are not particularly limited. The metal may be, for example, gold, silver, copper, tin, cobalt, iron, silicon, nickel, platinum, palladium, rhodium, or a rare metal, and the metal ion or metal complex ion may be an ion of these metals or a complex ion of these metals. Examples of a rare metal include strontium, manganese, cesium, and rare earths, and examples of rare earths include yttrium, scandium, and lutetium. The solution containing a metal ion or metal complex ion may contain one or more types of metal ions or metal complex ions. The metal ion or metal complex ion is preferably an ion or complex ion of at least one metal selected from the group consisting of gold, palladium, platinum, and rhodium, more preferably a gold complex ion or palladium complex ion, and still more preferably a gold complex ion. The metal may be a metal obtained by reducing these preferable metal ions or metal complex ions. That is, the metal is preferably at least one selected from the group consisting of gold, palladium, platinum, and rhodium, more preferably gold or palladium, and still more preferably gold. Examples of the gold complex ion include a tetrachloroaurate (III) ion ($[AuCl_3]^-$), dicyanoaurate (I) ion ($[Au(CN)_2]^-$), and $Au(HS)_2^-$. Examples of the palladium complex ion include a tetrachloropalladate (II) ion ($[PdCl_4]^{2-}$). Examples of the platinum complex ion include a hexachloroplatinate (IV) ion ($[PtCl_6]^{2-}$).

As described above, the produced metal may be crystallized metal atoms such as nanoparticulated metal, or may be non-crystallized metal atoms. In addition, the metal (particularly, metal nanoparticles) may be a metal whose surface is modified with a non-metal compound or a metal compound. In this specification, metals whose surfaces are modified are also included in the scope of "metal".

The concentration of the metal element (for example, the metal element to be recovered such as gold, palladium, platinum, and rhodium) in the solution containing a metal ion or metal complex ion is not particularly limited, and may be 10-3 to 105 ppm by mass. From the perspective of promoting sufficient nucleation and crystal growth necessary for the metal to take the form of nanoparticles, the concentration of the metal element is 0.001 ppm by mass or more, more preferably 0.01 ppm by mass or more, and still more preferably 0.1 ppm by mass or more. From the perspective of preventing the produced metal nanoparticles (for example, gold nanoparticles) from aggregating, the concentration of the metal element (for example, gold) is preferably less than 200 ppm by mass, more preferably 100 ppm by mass or less, and still more preferably 50 ppm by mass or less. In addition, from the perspective of increasing the amount of metal nanoparticles adsorbed to the blue-green alga, the concentration of the metal element may be, for example, 10,000 ppm by mass or less, 5,000 ppm by mass or less, 2,500 ppm by mass or less, 1,000 ppm by mass or less, 500 ppm by mass or less, 250 ppm by mass or less, 125 ppm by mass or less, or 50 ppm by mass or less and may be 12 ppm by mass or more or 25 ppm by mass or more. From the perspective of increasing the amount of metal nanoparticles adsorbed to the blue-green alga, the concentration of the metal element is preferably 12 to 250 ppm by mass, more preferably 12 to 125 ppm by mass, still more preferably 25 to 125 ppm by mass, and particularly preferably 25 to 50 ppm by mass.

The pH of the solution containing a metal ion or metal complex ion is not particularly limited, and may be, for example, −5 to 8.

The solution containing a metal ion or metal complex ion is not particularly limited, and examples thereof include electronic industry wastewater such as a plating waste solution, seawater, a solution of a metal element-containing substance (more specifically, a solution obtained by dissolving some or all of the metals or metal compounds contained in the metal element-containing substance), and a diluted solution thereof. The metal element-containing substance is not particularly limited as long as it is a substance containing a metal element, more specifically, one or more metals or metal compounds, and may be, for example, so-called urban mine such as an electronic board in waste electronic equipment. The metal element-containing substance preferably contains at least one selected from the group consisting of palladium, platinum, and rhodium, more preferably contains gold or palladium, and still more preferably contains gold.

Aqua regia is generally used to dissolve a metal element-containing substance, but since the oxidizing power of aqua regia is too high, when aqua regia is contained in a solution containing a metal ion or metal complex ion, it tends to dissolve even the blue-green alga contained in the metal recovery material. In addition, aqua regia not only damages the blue-green alga, but also shifts the chemical equilibrium in the solution containing a metal ion or metal complex ion, making it difficult for the reduction reaction of a metal ion or metal complex ion to occur. Therefore, when aqua regia is contained in a solution containing a metal ion or metal complex ion, the amount of metal to be adsorbed to the blue-green alga tends to decrease. More specifically, since hydrochloric acid contained in aqua regia has a high dissociation constant (low pKa), if the concentration of aqua regia increases (namely, the concentration of hydrochloric acid increases), the concentrations of hydrogen ion and chloride ion in the solution increase, and the chemical equilibrium shifts due to Le Chatelier's principle. As a result, it becomes difficult for a metal ion or metal complex ion to exist in an ionic state and to be reduced by the blue-green alga in the solution (for example, in the case of tetrachloroauric acid, HAuCh becomes less likely to ionize to H and $[AuCl_4]^-$). Therefore, from the perspective of reducing the dissolution of the blue-green alga and from the perspective of increasing the amount of metal to be adsorbed to the blue-green alga, it is preferable that the solution containing a metal ion or metal complex ion does not contain a combination of hydrochloric acid and nitric acid or does not contain aqua regia. In this specification, aqua regia is a solution obtained by mixing concentrated hydrochloric acid (35 mass % hydrochloric acid) and concentrated nitric acid (60 mass % nitric acid) at a volume ratio of 3:1. When the solution containing a metal ion or metal complex ion contains aqua regia, from the perspective of reducing the dissolution of the blue-green alga and from the perspective of increasing the amount of metal to be adsorbed to the blue-green alga, the concentration of aqua regia is preferably 5 mass % (1.3 mass % of hydrochloric acid and 0.75 mass % of nitric acid) or less, more preferably 2 mass % (0.53 mass % of hydrochloric acid and 0.30 mass % of nitric acid) or less, and still more preferably 1 mass % (0.26 mass % of hydrochloric acid and 0.15 mass % of nitric acid) or less. Therefore, in the solution containing a metal ion or metal complex ion, preferably, the concentration of hydrochloric acid is 1.3 mass % or less and the concentration of nitric acid is 0.75 mass % or less, more preferably, the concentration of hydrochloric acid is 0.53 mass % or less and the concentration of nitric acid is 0.30 mass % or less, and still more preferably, the concentration of hydrochloric acid is 0.26 mass % or less and the concentration of nitric acid is 0.15 mass % or less. From the perspective of reducing the dissolution of the blue-green alga and from the perspective of increasing the amount of metal to be adsorbed to the blue-green alga, the concentration of hydrochloric acid in the solution containing a metal ion or metal complex ion is preferably 20 mass % or less, 15 mass % or less, 10 mass % or less, 5 mass % or less, 2.6 mass % or less, 1.3 mass % or less, 1 mass % or less, 0.53 mass % or less, or 0.26 mass % or less, and it is preferable that the solution containing a metal ion or metal complex ion does not contain hydrochloric acid.

In one embodiment, the solution containing a metal ion or metal complex ion is a solution (that is, solution of the metal element-containing substance) obtained by bringing a metal element-containing substance into contact with a dissolving solution containing nitric acid and a salt to dissolve a part or all of the metal element-containing substance (more specifically, metals or metal compounds contained in the metal element-containing substance). Aqua regia (concentrated hydrochloric acid:concentrated nitric acid=3:1 (volume ratio)) is generally used to dissolve the metal element-containing substance, but since the oxidizing power of aqua regia is too high, it tends to dissolve even the blue-green alga contained in the metal recovery material. In addition, when a solution obtained by treating a metal element-containing substance with aqua regia is neutralized, dissolved substances other than metals contained in the metal element-containing substance precipitate and the viscosity tends to become high. Meanwhile, according to the present embodiment, since the oxidizing power does not become excessively high, the metal element-containing substance can be dissolved while suppressing the dissolution of the blue-green alga. In addition, while the present inventors found that, when aqua regia is used to dissolve the metal element-containing substance, the dissolution of the blue-green alga is suppressed by diluting aqua regia before the metal recovery material is immersed, according to the present embodiment in which a dissolving solution containing nitric acid and a salt is used, such a dilution step is unnecessary.

The salt contained in the dissolving solution containing nitric acid and a salt is not particularly limited as long as it is a salt that can increase the oxidizing power by using in combination with nitric acid, and examples thereof include alkali metal salts, alkaline earth metal salts, and aluminum salts. The salt is preferably a halide, and more preferably a chloride. Examples of the chloride include sodium chloride, magnesium chloride, potassium chloride, lithium chloride, calcium chloride, and aluminum chloride. The dissolving solution containing nitric acid and a salt may contain one or more salts. The dissolving solution containing nitric acid and a salt may be, for example, seawater, artificial seawater, or bittern containing nitric acid.

From the perspective of rapidly dissolving the metal element-containing substance, the concentration of nitric acid in the dissolving solution containing nitric acid and a salt is preferably 2 mass % or more, and more preferably 3 mass % or more. From the perspective of reducing the dissolution of the blue-green alga, the concentration of nitric acid in the dissolving solution containing nitric acid and a salt is preferably 50 mass % or less, 40 mass % or less, 30 mass % or less, 20 mass % or less, 10 mass % or less, or 5 mass % or less.

From the perspective of rapidly dissolving the metal element-containing substance, the total salt concentration in the dissolving solution containing nitric acid and a salt is preferably 0.5 mass % or more, 1 mass % or more, 2 mass % or more, 3 mass % or more, 4 mass % or more, 6 mass % or more, 8 mass % or more, 10 mass % or more, or 20 mass % or more. From the perspective of facilitating the refining of the produced metals, the total salt concentration in the dissolving solution containing nitric acid and a salt may be, for example, 50 mass % or less, 40 mass % or less, 30 mass % or less, 20 mass % or less, 10 mass % or less, 8 mass % or less, 6 mass % or less, 4 mass % or less, 3 mass % or less, 2 mass % or less, or 1 mass % or less. The higher the total salt concentration in the dissolving solution containing nitric acid and a salt, the shorter the time it takes to dissolve the metal element-containing substance, although the cost of refining the produced metals tends to be higher. From the perspective of rapidly dissolving the metal element-containing substance while reducing the refining cost of the produced metals, the total salt concentration in the dissolving solution containing nitric acid and a salt is preferably 1 to 10 mass %.

The dissolving solution containing nitric acid and a salt may contain, for example, 2 to 50 mass % of nitric acid and 0.5 mass % or more of salt, 2 to 20 mass % of nitric acid and 0.5 mass % or more of salt, 3 to 20 mass % of nitric acid and 0.5 mass % or more of salt, or 3 to 10 mass % of nitric acid and 1 to 10 mass % or more of salt.

From the perspective of rapidly dissolving the metal element-containing substance, the ratio of the mass of nitric acid in the dissolving solution containing nitric acid and a salt to the mass of the metal contained in the metal element-containing substance (hereinafter referred to as a nitric acid/metal ratio) is preferably 100 or more, and more preferably 150 or more. From the perspective of reducing the dissolution of the blue-green alga, the nitric acid/metal ratio is preferably 2,500 or less, 2,000 or less, 1,500 or less, 1,000 or less, 500 or less, or 250 or less.

From the perspective of rapidly dissolving the metal element-containing substance, the ratio of the total mass of the salt in the dissolving solution containing nitric acid and a salt to the mass of the metal contained in the metal element-containing substance (hereinafter referred to as a salt/metal ratio) is preferably 25 or more, 50 or more, 100 or more, 150 or more, 200 or more, 300 or more, 400 or more, 500 or more, or 1,000 or more. From the perspective of facilitating refining of the produced metals, the salt/metal ratio may be, for example, 2,500 or less, 2,000 or less, 1,500 or less, 1,000 or less, 500 or less, 400 or less, 300 or less, 200 or less, 150 or less, 100 or less, or 50 or less. The higher the salt/metal ratio in the dissolving solution containing nitric acid and a salt, the shorter the time it takes to dissolve the metal element-containing substance, although the cost of refining the produced metals tends to be higher. From the perspective of rapidly dissolving the metal element-containing substance while reducing the refining cost of the produced metals, the salt/metal ratio is preferably 50 to 500.

The pH of the dissolving solution containing nitric acid and a salt is not particularly limited, and may be, for example, −5 to 8.

From the perspective of reducing the dissolution of the blue-green alga and from the perspective of increasing the amount of metal to be adsorbed to the blue-green alga, it is preferable that the dissolving solution containing nitric acid and a salt does not contain aqua regia. From the perspective of reducing the dissolution of the blue-green alga and from the perspective of increasing the amount of metal to be adsorbed to the blue-green alga, the concentration of hydrochloric acid in the dissolving solution containing nitric acid and a salt is preferably 20 mass % or less, 15 mass % or less, 10 mass % or less, 5 mass % or less, 2.6 mass % or less, 1.3 mass % or less, 1 mass % or less, 0.53 mass % or less, or 0.26 mass % or less, and it is preferable that the dissolving solution containing nitric acid and a salt does not contain hydrochloric acid.

The solution containing a metal ion or metal complex ion obtained by bringing the metal element-containing substance into contact with the dissolving solution containing nitric acid and a salt contains nitric acid and a salt at the above concentration.

In another embodiment, the solution containing a metal ion or metal complex ion may be a solution obtained by a method including steps of: bringing a metal element-containing substance into contact with a dissolving solution containing 10 mass % or more of aqua regia to obtain a solution of the metal element-containing substance; and diluting the solution of the metal element-containing substance such that the concentration of aqua regia becomes 5 mass % or less. As described above, since the oxidizing power of aqua regia, which is generally used to dissolve the metal element-containing substance, is too high, it tends to dissolve even the blue-green alga contained in the metal recovery material, and also, aqua regia shifts the chemical equilibrium in the solution containing a metal ion or metal complex ion, making it difficult for the reduction reaction of a metal ion or metal complex ion to occur. Meanwhile, in the present embodiment, the dissolution of the blue-green alga can be suppressed and reduction in the amount of metal to be adsorbed to the blue-green alga can be suppressed, by diluting the solution of the metal element-containing substance such that the concentration of aqua regia becomes 5 mass % or less, prior to immersing the metal recovery material in the solution of the metal element-containing substance.

The concentration of aqua regia in the dissolving solution containing aqua regia is not particularly limited as long as the metal element-containing substance can be dissolved, and may be, for example, 10 mass % or more or 30 mass % or more, and the dissolving solution containing aqua regia may be 100% aqua regia.

From the perspective of reducing the dissolution of the blue-green alga and from the perspective of increasing the amount of metal to be adsorbed to the blue-green alga, the concentration of aqua regia in the diluted solution (solution containing a metal ion or metal complex ion) of the metal element-containing substance is preferably 5 mass % or less, more preferably 2 mass % or less, and still more preferably 1 mass % or less.

A method for recovering a metal from a solution containing a metal ion or metal complex ion according to one aspect of the present disclosure includes a step of immersing a blue-green alga in a solution containing a metal ion or metal complex ion to produce a metal, and the blue-green alga is a blue-green alga of the genus *Leptolyngbya*. Details of the solution containing a metal ion or metal complex ion, the blue-green alga, and the metal to be produced are as described above. As described above, when the blue-green alga of the genus *Leptolyngbya* is immersed in the solution containing a metal ion or metal complex ion, the blue-green alga reduces the metal ion or metal complex ion to produce a metal atom. The produced metal atom is adsorbed onto the blue-green alga, and certain metal atoms such as gold, palladium, platinum, and rhodium crystallize to form nanoparticles. The nanoparticulated metal remains adsorbed to the blue-green alga or is released from the blue-green alga into the solution.

The ratio of the mass of the blue-green alga to the mass of the metal element (for example, the metal element to be recovered such as gold, palladium, platinum, and rhodium) in the solution containing a metal ion or metal complex ion (hereinafter referred to as an alga/metal ratio) is not particularly limited, and may be, for example, 0.1 to 10,000. From the perspective of increasing the amount of metal to be adsorbed to the blue-green alga, the alga/metal ratio may be, for example, 4 or more, 9 or more, 10 or more, 40 or more, 111 or more, 120 or more, 185 or more, 200 or more, or 1,000 or more. The upper limit of the alga/metal ratio is not particularly limited, and the alga/metal ratio may be, for example, 10,000 or less, 2,000 or less, 1,000 or less, 300 or less, 200 or less, 120 or less, 111 or less, 100 or less, 40 or less, or 9 or less. The higher the alga/metal ratio, the more the amount of metal to be adsorbed to the blue-green alga increases, although the cost also rises due to the increased amount of the blue-green alga used. From the perspective of increasing the amount of metal to be adsorbed to the blue-green alga while reducing the cost of blue-green alga, the alga/metal ratio is preferably 9 to 1,000, more preferably 9 to 300, still more preferably 9 to 100, and particularly preferably 9 to 30.

When a metal ion or metal complex ion of gold and/or palladium and a metal ion or metal complex ion of rhodium and/or platinum are contained in the solution containing a metal ion or metal complex ion, from the perspective of selectively adsorbing gold and/or palladium to the blue-green alga, the ratio of the mass of blue-green alga to the mass of rhodium in the solution containing a metal ion or metal complex ion is preferably 11 or less, and the ratio of the mass of blue-green alga to the mass of platinum in the solution containing a metal ion or metal complex ion is preferably 16 or less.

The amount of the blue-green alga to be immersed in the solution containing a metal ion or metal complex ion may be determined as appropriate depending on the concentrations of metal elements in the solution, but from the perspective of getting the reduction reaction of a metal ion or metal complex ion to proceed, preferably 0.2 mg or more, more preferably 2 mg or more, still more preferably 3 mg or more, and particularly preferably 20 mg or more of the blue-green alga is immersed with respect to 100 mL of the solution containing a metal ion or metal complex ion.

The temperature at which the blue-green alga is immersed in a solution containing a metal ion or metal complex ion is not particularly limited, and may be, for example, 0 to 100° C. From the perspective of reducing the release of the metal nanoparticles from the blue-green alga and increasing the amount of metal nanoparticles adsorbed to the blue-green alga, the temperature during the immersion is preferably 10 to 100° C., more preferably 50 to 100° C., and still more preferably 70 to 100° C. The temperature during the immersion may be, for example, 10 to 50° C., 51 to 70° C., or 71 to 100° C. On the other hand, from the perspective of increasing the amount of metal nanoparticles released into the solution (that is, from the perspective of increasing the concentration of the metal colloidal solution to be described below), the temperature during the immersion is preferably 0 to 75° C., more preferably 0 to 50° C., and still more preferably 0 to 30° C.

From the perspective of getting the reduction reaction of the metal ion or metal complex ion to proceed sufficiently, the time for immersing the blue-green alga in the solution containing a metal ion or metal complex ion may be, for example, 0.5 hours or longer, 1 hour or longer, 3 hours or longer, 8 hours or longer, or 24 hours or longer. The upper limit of the time for immersing the blue-green alga in the solution containing a metal ion or metal complex ion is not particularly limited, and may be, for example, 100 hours or shorter, 48 hours or shorter, 24 hours or shorter, 8 hours or shorter, 3 hours or shorter, or 1 hour or shorter. If the time for immersing the blue-green alga in the solution containing a metal ion or metal complex ion is 1 to 8 hours, it can be said to be sufficiently short and a high recovery ratio can also be achieved.

The immersion of the blue-green alga in the solution containing a metal ion or metal complex ion may be performed under light irradiation or while blocking light. By irradiating the solution containing a metal ion or metal complex ion (and a blue-green alga in the solution) with light, it is possible to reduce the release of the metal nanoparticles from the blue-green alga and maintain more metal nanoparticles in a state of being adsorbed to the blue-green alga. In this case, the light for irradiating the solution containing a metal ion or metal complex ion may be visible light or ultraviolet light, and may be, for example, natural light (sunlight). From the perspective of reducing the release of the metal nanoparticles from the blue-green alga and increasing the amount of metal nanoparticles adsorbed to the blue-green alga, the light for irradiating the solution containing a metal ion or metal complex ion is a light with a wavelength of preferably 800 nm or less (for example, white light of 435 to 800 nm), more preferably 545 nm or less (for example, green light of 495 to 545 nm), still more preferably 490 nm or less (for example, blue light of 435 to 490 nm), and particularly preferably 400 nm or less (for example, ultraviolet light of 350 to 400 nm). The irradiation intensity with a light may be 10 to 1,000 mW or 100 to 1,000 mW with respect to 100 mL of the solution containing a metal ion or metal complex ion. In this specification, mW is a unit indicating a radiant flux intensity. On the other hand, by blocking the solution containing a metal ion or metal complex ion (and a blue-green alga in the solution) from light, the amount of metal nanoparticles released from the blue-green alga into the solution can be increased. In this case, from the perspective of increasing the amount of metal nanoparticles released into the solution, the immersion of the blue-green alga in the solution containing a metal ion or metal complex ion is performed while blocking light with a wavelength of preferably 800 nm or less, more preferably 545 nm or less, still more preferably 490 nm or less, and particularly preferably 400 nm or less (namely, ultraviolet light).

While immersing the blue-green alga in the solution containing a metal ion or metal complex ion, it is preferable to stir the solution containing a metal ion or metal complex ion. The rotational speed for stirring is not particularly limited, and may be, for example, 100 to 1,000 rpm.

The method for recovering a metal from a solution containing a metal ion or metal complex ion according to the present aspect of the present disclosure may further include a step of recovering the produced metal (adsorbed to the blue-green alga or dispersed in the solution). The method for recovering the metal is not particularly limited, and may be appropriately selected depending on a desired form, a desired purity and the like of the metal to be recovered. The recovery of metal may be performed, for example, by separating (or recovering) the blue-green alga from the solution in which the blue-green alga has been immersed and recovering the remaining solution (metal colloidal solution), or by recovering the metal from the recovered blue-green alga.

The metal in the obtained metal colloidal solution may be recovered by centrifuging the metal colloidal solution to concentrate the metal or by adding a flocculant (for example, sea salt, NaCl, $MgCl_2$, etc.) to the metal colloidal solution to precipitate the metal.

In order to separate (or recover) the blue-green alga from the solution in which the blue-green alga has been immersed, the step of recovering the metal may include a step of filtering the solution in which the blue-green alga has been immersed. When metal nanoparticles are contained in the solution in which the blue-green alga has been immersed, a filtrate containing the metal nanoparticles, namely, a metal colloidal solution can be obtained by this step. Metal atoms can be released from the blue-green alga into the solution only when they are nanoparticulated, and metal atoms that are not crystallized are not released from the blue-green alga. Therefore, even when both an ion or complex ion of a metal that can crystallize to form nanoparticles on the blue-green alga (for example, gold, palladium, platinum, and rhodium) and an ion or complex ion of a metal that cannot form nanoparticles on the blue-green alga are contained in the solution containing a metal ion or metal complex ion, only a metal that can form nanoparticles can be selectively recovered by this step.

In one embodiment, the step of recovering the metal may further include a step of ultrasonicating the blue-green alga. The ultrasonication may be performed before separating the blue-green alga from the solution in which the blue-green alga has been immersed (namely, for example, before the filtration step) or may be performed after recovering the blue-green alga from the solution in which the blue-green alga has been immersed and resuspending the blue-green alga in a liquid. By ultrasonicating the blue-green alga, the metal nanoparticles adsorbed to the blue-green alga can be easily desorbed from the blue-green alga, while non-crystallized metal atoms do not desorb from the blue-green alga. Therefore, when metal nanoparticles and non-crystallized metal atoms are adsorbed to the blue-green alga, by ultrasonicating the solution in which the blue-green alga has been immersed or suspended, the metal nanoparticles are released into the solution and the non-crystallized metal atoms remain adsorbed to the blue-green alga, and thus the metal nanoparticles and the non-crystallized metal atoms can be separated. Namely, according to this step, metals that can form nanoparticles on the blue-green alga can be selectively recovered and metals that cannot form nanoparticles on the blue-green alga can also be selectively recovered. Conditions of ultrasonication are not particularly limited, and for example, the blue-green alga may be treated with ultrasonic waves of 20 to 100 kHz for 10 to 60 minutes.

In one embodiment, the step of recovering the metal may include steps of: ultrasonicating the solution in which the blue-green alga has been immersed; and filtering the ultrasonicated solution. According to this embodiment, a filtrate containing more metal nanoparticles, namely, a metal colloidal solution of higher concentration can be obtained, compared to when the solution in which the blue-green alga has been immersed is not ultrasonicated. In addition, in another embodiment, the step of recovering the metal may include steps of: filtering the solution in which the blue-green alga has been immersed; and ultrasonicating the blue-green alga after filtration. The ultrasonication can be performed by suspending the recovered blue-green alga in an arbitrary liquid such as water or an aqueous solution and ultrasonicating the suspension. By filtering the ultrasonicated suspension, a filtrate containing metal nanoparticles, namely, a metal colloidal solution can be obtained. The solution in which the blue-green alga has been immersed may contain components other than metal nanoparticles (for example, metal ions or metal complex ions that remain unreduced) along with the produced metal nanoparticles, but in the present embodiment, a metal colloidal solution of higher purity can be obtained, because the metal nanoparticles adsorbed to the blue-green alga are recovered after the blue-green alga is recovered from the solution in which the blue-green alga has been immersed by filtration.

In one embodiment, the step of recovering the metal may further include a step of firing the recovered blue-green alga, in order to recover the metal from the recovered blue-green alga. By this step, the blue-green alga itself is removed, and the metal adsorbed to the blue-green alga can be recovered. In addition, before firing the blue-green alga, the blue-green alga may be molded into a desired shape. This makes it possible to obtain a metal molded product of the desired shape by firing the blue-green alga. Firing can be easily performed in, for example, air. The firing temperature is not particularly limited, and may be selected as appropriate depending on the melting point of the metal. The firing temperature may be, for example, 800 to 1,200° C. The firing temperature may be constant or may be increased in stages. For example, the blue-green alga may first be heated for a certain period of time at a temperature at which the blue-green alga burns, and then, the heating may be continued at a temperature near the melting point of the metal in order to increase the crystallinity of the metal.

In the method for recovering a metal from a solution containing a metal ion or metal complex ion according to the present aspect of the present disclosure, recovery of the metal from the solution containing a metal ion or metal complex ion may be performed only once or may be performed a plurality of times in a divided manner. Namely, in one embodiment, the method for recovering a metal from a solution containing a metal ion or metal complex ion may include steps of:

(i) immersing a blue-green alga in a solution containing a metal ion or metal complex ion to produce a metal and to adsorb the metal onto the blue-green alga;

(ii) recovering the blue-green alga to which the metal has been adsorbed; and (iii) recovering the metal from the recovered blue-green alga, and the step (i) of immersing a blue-green alga and the step (ii) of recovering the blue-green alga may be performed twice or more. Here, the blue-green algae used for the second and subsequent immersions are blue-green algae different from the blue-green alga recovered from the solution containing a metal ion or metal complex ion. In other words, a blue-green alga that has been used once is not used again, and a new blue-green alga is always used for adsorbing the metal.

Details of the step (i) of immersing a blue-green alga in a solution containing a metal ion or metal complex ion to produce a metal and to adsorb the metal onto the blue-green alga are the same as in the above step of immersing a blue-green alga in a solution containing a metal ion or metal complex ion to produce a metal. However, the alga/metal ratio is preferably 0.1 to 1,100. In addition, the temperature at which the blue-green alga is immersed in a solution containing a metal ion or metal complex ion is preferably adjusted to a temperature at which it is possible to reduce the release of the metal nanoparticles from the blue-green alga and increase the amount of metal nanoparticles adsorbed to the blue-green alga. That is, the temperature during the immersion is preferably 10 to 100° C., more preferably 50 to 100° C., and still more preferably 70 to 100° C. In addition, in order to reduce the amount of metal nanoparticles released from the blue-green alga and increase the amount of metal nanoparticles adsorbed to the blue-green alga, the solution containing a metal ion or metal complex ion may be irradiated with light with a wavelength of preferably 800 nm or less, more preferably 545 nm or less, still more preferably 490 nm or less, and particularly preferably 400 nm or less (namely, ultraviolet light).

The method for recovering the blue-green alga to which the metal has been adsorbed is not particularly limited, and for example, by filtering the solution containing a metal ion or metal complex ion in which the blue-green alga has been immersed, the blue-green alga may be recovered from the solution.

The metal adsorbed to the blue-green alga can be recovered by the above method, that is, by firing the blue-green alga or by ultrasonicating the blue-green alga. Details of these methods are as described above. The step (iii) of recovering the metal from the blue-green alga may be performed at an arbitrary stage and an arbitrary number of times. For example, the step (iii) of recovering the metal from the blue-green alga may be performed whenever the step (ii) of recovering the blue-green alga is performed, or may be performed only once after the step (ii) of recovering the final blue-green alga.

As shown in Test Example 13 to be described below, the higher the alga/metal ratio, the larger the amount of metal that can be adsorbed with each step (i) of immersing a blue-green alga, and the fewer the number of repetitions of the above steps (i) and (ii) needed to achieve a predetermined recovery ratio (for example, 80%). However, the higher the alga/metal ratio, the lower the utilization efficiency of the blue-green alga (for example, the mass of metal that can be recovered per unit mass of the blue-green alga may be used as an indicator) becomes, and thus, compared to when the steps (i) and (ii) are repeated many times at a low alga/metal ratio, more blue-green alga is needed to achieve a predetermined recovery ratio and the cost of the blue-green alga becomes higher. Therefore, from the perspective of reducing the cost of the blue-green alga while reducing the number of repetitions of the steps (i) and (ii), the steps (i) and (ii) are preferably performed 1 to 30 times at an alga/metal ratio of 3 to 1,100, more preferably performed 2 to 10 times at an alga/metal ratio of 20 to 400, and still more preferably performed 3 to 5 times at an alga/metal ratio of 40 to 100.

According to one embodiment of the method for recovering a metal from a solution containing a metal ion or metal complex ion, by using a solution containing a gold ion or gold complex ion as the solution containing a metal ion or metal complex ion, gold can be recovered in the form of gold nanoparticles. Therefore, one aspect of the present disclosure provides a method for producing gold nanoparticles including a step of immersing a blue-green alga in a solution containing a gold ion or gold complex ion to produce gold nanoparticles. The blue-green alga is a blue-green alga of the genus *Leptolyngbya*, and details of the blue-green alga are as described above.

Details of the solution containing a gold ion and gold complex ion are the same as in the above solution containing a metal ion or metal complex ion, except that it always contains at least a gold ion or gold complex ion as the metal ion or metal complex ion. Namely, the solution containing a gold ion or gold complex ion may contain metal ions or metal complex ions other than the gold ion or gold complex ion. The solution containing a gold ion or gold complex ion preferably contains substantially only the gold ion or gold complex ion as the metal ion or metal complex ion. The solution containing a gold ion or gold complex ion may be, for example, an aqueous tetrachloroauric acid solution.

Details of the step of immersing a blue-green alga in a solution containing a gold ion or gold complex ion to produce gold nanoparticles are the same as in the above step of immersing a blue-green alga in a solution containing a metal ion or metal complex ion to produce a metal.

The method for producing gold nanoparticles may further include a step of recovering the produced gold nanoparticles. Details of the step of recovering the produced gold nanoparticles are the same as in the above step of recovering the produced metal.

According to one embodiment of the above method for recovering a metal from a solution containing a metal ion or metal complex ion, the metal can be recovered in the form of a metal molded product by adsorbing the metal onto the blue-green alga and then recovering, molding, and firing the blue-green alga. Therefore, one aspect of the present disclosure provides a method for producing a metal molded product. The method for producing a metal molded product includes steps of: immersing a blue-green alga in a solution containing a metal ion or metal complex ion to produce a metal and to adsorb the metal onto the blue-green alga; recovering the blue-green alga to which the metal has been adsorbed; molding the recovered blue-green alga; and firing the molded blue-green alga to obtain a metal molded product.

Details of the solution containing a metal ion or metal complex ion and the blue-green alga are as described above. Details of the step of immersing a blue-green alga in a solution containing a metal ion or metal complex ion to produce a metal and to adsorb the metal onto the blue-green alga are the same as in the above step of immersing a blue-green alga in a solution containing a metal ion or metal complex ion to produce a metal. However, the temperature at which the blue-green alga is immersed in a solution containing a metal ion or metal complex ion is preferably adjusted to a temperature at which it is possible to reduce the release of the metal nanoparticles from the blue-green alga and increase the amount of metal nanoparticles adsorbed to the blue-green alga. That is, the temperature during the immersion is preferably 10 to 100° C., more preferably 50 to 100° C., and still more preferably 70 to 100° C. In addition, in order to reduce the release of the metal nanoparticles from the blue-green alga and increase the amount of metal nanoparticles adsorbed to the blue-green alga, the solution containing a metal ion or metal complex ion may be irradiated with light with a wavelength of preferably 800 nm or less, more preferably 545 nm or less, still more preferably 490 nm or less, and particularly preferably 400 nm or less (namely, ultraviolet light).

The method for recovering the blue-green alga to which the metal has been adsorbed is not particularly limited, and for example, by filtering the solution in which the blue-green alga has been immersed, the blue-green alga may be recovered from the solution.

In the step of molding the recovered blue-green alga, the blue-green alga is molded into a desired shape (for example, a star shape or a heart shape). The method for molding the blue-green alga is not particularly limited, and for example, blue-green alga can be molded by placing the blue-green alga in a mold having a desired shape.

The firing conditions in the step of firing the molded blue-green alga may be the same as the above firing conditions.

The metal molded product may be for personal ornaments. That is, the produced metal molded product can be used as personal ornaments such as necklaces and earrings.

A method for recovering a metal from a solution containing a metal ion or metal complex ion according to another aspect of the present disclosure includes bringing a blue-green alga extract solution into contact with a solution containing a metal ion or metal complex ion to produce a metal, and the blue-green alga is a blue-green alga of the genus *Leptolyngbya*. As described above, the blue-green alga of the genus *Leptolyngbya* has an ability to reduce the metal ion or metal complex ion in the solution containing a metal ion or metal complex ion to produce a metal atom. The present inventors found that an extract solution of such a blue-green alga also has the same reducing effect. Namely, by bringing the extract solution of a blue-green alga of the genus *Leptolyngbya* into contact with a solution containing a metal ion or metal complex ion, the metal ion or metal complex ion in the solution can be recovered as a solid metal (including in the form of a metal colloidal solution). This method has an advantage that the reduction reaction can be entirely performed in a wet manner (that is, in a solution) without using a solid blue-green alga.

The blue-green alga of the genus *Leptolyngbya* may be, for example, a blue-green alga of the genus *Leptolyngbya* deposited to The National Institute of Technology and Evaluation, International Patent Organism Depositary (IPOD) (#120, 2-5-8 Kazusakamatari, Kisarazu-shi, Chiba 292-0818, Japan) with accession number FERM BP-22385 (original deposit date: Jan. 17, 2020).

The blue-green alga extract solution may be an extract solution of a dried product of the blue-green alga, more specifically a dried product in the form of powder. The blue-green alga extract solution may be an extract solution of a blue-green alga treated with an acid. Here, treating the blue-green alga with an acid specifically means immersing the blue-green alga, preferably a blue-green alga washed with water, in an acid. By treating the blue-green alga with an acid, metal elements (Fe, Cu, B, Ca, P, Mg, K, Sr, Mn, Ba, etc.) constituting the blue-green alga are removed from the blue-green alga, and the reducing ability of the reducing substance contained in the blue-green alga is improved. Therefore, an extract solution containing a reducing substance with a higher reducing ability can be obtained. The acid is not particularly limited, and may be, for example, hydrochloric acid, nitric acid, sulfuric acid, or any combination thereof.

The time for acid treatment (that is, the time for immersion in an acid) is not particularly limited, and may be, for example, 5 minutes to 120 minutes, and is desirably 10 minutes to 60 minutes.

The extract solution may be prepared, for example, by immersing the blue-green alga in an organic solvent and then removing the blue-green alga by filtration. The organic solvent is not particularly limited, and may be, for example, ethanol, acetone, or dichloromethane. The extraction time is preferably 1 hour or longer, and may be, for example, 24 hours. Extraction is preferably performed while stirring the organic solvent at, for example, 500 rpm. The ratio of the blue-green alga and the organic solvent may be, for example, 0.1 to 10,000 mL, 1 to 1,000 mL, or 10 to 100 mL of the organic solvent with respect to 1 g of the blue-green alga.

The metal ion, metal complex ion, and a metal to be produced and recovered from these ions are not particularly limited. The metal may be, for example, gold, silver, copper, tin, cobalt, iron, silicon, nickel, platinum, palladium, rhodium, or a rare metal, and the metal ion or metal complex ion may be an ion of these metals or a complex ion of these metals. Examples of a rare metal include strontium, manganese, cesium, and rare earths, and examples of rare earths include yttrium, scandium, and lutetium. The solution containing a metal ion or metal complex ion may contain one or more types of metal ions or metal complex ions. The metal ion or metal complex ion is preferably an ion or complex ion of at least one metal selected from the group consisting of gold, palladium, platinum, and rhodium, more preferably a gold complex ion, palladium complex ion, or platinum complex ion, and still more preferably a gold complex ion. The metal may be a metal obtained by reducing these preferable metal ions or metal complex ions. That is, the metal is preferably at least one selected from the group consisting of gold, palladium, platinum, and rhodium, more preferably gold, palladium, or platinum, and still more preferably gold. Examples of the gold complex ion include a tetrachloroaurate (III) ion ($[AuCl_4]^-$), dicyanoaurate (I) ion ($[Au(CN)_2]^-$), and $Au(HS)_2$. Examples of the palladium complex ion include a tetrachloropalladate (II) ion ($[PdCl_4]^{2-}$). Examples of the platinum complex ion include a hexachloroplatinate (IV) ion ($[PtCl_6]^{2-}$).

The concentration of the metal element (for example, the metal element to be recovered such as gold, palladium, platinum, and rhodium) in the solution containing a metal ion or metal complex ion is not particularly limited, and may be 10-3 to 105 ppm by mass or 1 to 1,000 ppm. From the perspective of promoting sufficient nucleation and crystal growth necessary for the metal to take the form of nanoparticles, the concentration of the metal element is 0.001 ppm by mass or more, more preferably 0.01 ppm by mass or more, and still more preferably 0.1 ppm by mass or more. From the perspective of preventing the produced metal nanoparticles (for example, gold nanoparticles) from aggregating, the concentration of the metal element (for example, gold) is preferably less than 200 ppm by mass, more preferably 100 ppm by mass or less, and still more preferably 50 ppm by mass or less.

The solution containing a metal ion or metal complex ion is not particularly limited, and examples thereof include electronic industry wastewater such as a plating waste solution, seawater, a solution of a metal element-containing substance (more specifically, a solution obtained by dissolving some or all of the metals or metal compounds contained in the metal element-containing substance), and a diluted solution thereof. The metal element-containing substance is not particularly limited as long as it is a substance containing a metal element, more specifically, one or more metals or metal compounds, and may be, for example, so-called urban mine such as an electronic board in waste electronic equipment. The metal element-containing substance preferably contains at least one selected from the group consisting of palladium, platinum, and rhodium, more preferably contains gold or palladium, and still more preferably contains gold.

The ratio of the mass of the blue-green alga extract solution to the mass of the metal element (for example, the metal element to be recovered such as gold, palladium, platinum, and rhodium) in the solution containing a metal ion or metal complex ion (hereinafter referred to as an alga extract solution/metal ratio) is not particularly limited, and may be, for example, 1 to 1,000,000, 10 to 100,000, 10 to 10,000, or 100 to 1,000.

The amount of the extract solution to be brought into contact with the solution containing a metal ion or metal complex ion may be determined as appropriate depending on the amount of the blue-green alga used to prepare the extract solution and on the concentrations of metal elements in the solution, and may be, for example, 0.01 to 1,000 mL, 0.1 to 100 mL, or 1 to 10 mL with respect to 1 mL of the solution containing a metal ion or metal complex ion.

The temperature at which the blue-green alga extract solution is in contact with the solution containing a metal ion or metal complex ion is not particularly limited, and may be, for example, 0 to 100° C., 10 to 70° C., or 30 to 60° C.

From the perspective of getting the reduction reaction of the metal ion or metal complex ion to proceed sufficiently, the time for which the blue-green alga extract solution is brought into contact with the solution containing a metal ion or metal complex ion may be, for example, 0.5 hours or longer, 1 hour or longer, 3 hours or longer, 8 hours or longer, or 24 hours or longer. The upper limit of the time for which the blue-green alga extract solution is brought into contact with the solution containing a metal ion or metal complex ion is not particularly limited, and may be, for example, 100 hours or shorter, 48 hours or shorter, 24 hours or shorter, 8 hours or shorter, 3 hours or shorter, or 1 hour or shorter.

While the blue-green alga extract solution is in contact with the solution containing a metal ion or metal complex ion, it is preferable to stir the solution containing a metal ion or metal complex ion. The rotational speed for stirring is not particularly limited, and may be, for example, 100 to 1,000 rpm.

The method for recovering a metal from a solution containing a metal ion or metal complex ion according to the present aspect of the present disclosure may further include a step of recovering the produced metal. The method for recovering the metal is not particularly limited, and for example, the solution containing a metal ion or metal complex ion after being brought into contact with the blue-green alga extract solution (that is, the solution containing the produced metal) may be directly recovered as a metal colloidal solution. Alternatively, the solution containing the produced metal may be centrifuged to recover the concentrated metal. In addition, the metal may be recovered by adding a flocculant (for example, sea salt, NaCl, $MgCl_2$, etc.) to the solution containing the produced metal to precipitate the metal.

As described above, according to the present disclosure, it is possible to recover metals in a desired form, for example, from urban mines so that it can contribute to achieve Goal 12 of sustainable development goals (SDGs), "Ensure sustainable consumption and production patterns".

EXAMPLES

In the following test examples, all ppm are ppm by mass, and the alga/Au ratio, the alga/Rh ratio, and the alga/Pt ratio are the ratio of the mass of blue-green alga to the mass of gold, rhodium, and platinum, respectively. Unless otherwise stated, the following test examples were performed at room temperature (RT) of 20 to 30° C. under indoor lighting with a white light emitting diode (LED) (465 to 800 nm). In the following test examples, artificial seawater is water (salt concentration: 3.8 mass %) in which Marine Art SF-1 (commercially available from Osaka Yakken Co., Ltd.) is dissolved. Components contained in Marine Art SF-1 are as follows: sodium chloride, calcium chloride, potassium chloride, potassium bromide, anhydrous strontium chloride, lithium chloride, manganese chloride, aluminum chloride, sodium tungstate, magnesium chloride, anhydrous sodium sulfate, sodium bicarbonate, borax, sodium fluoride, potassium iodide, cobalt chloride, ferric chloride, and ammonium molybdate.

<Preparation of Blue-Green Alga>

In the following test examples, a dry powder of a blue-green alga of the genus *Leptolyngbya* deposited to The National Institute of Technology and Evaluation, International Patent Organism Depositary (IPOD) (#120, 2-5-8 Kazusakamatari, Kisarazu-shi, Chiba 292-0818, Japan) with accession number FERM BP-22385 (original deposit date: Jan. 17, 2020) was used as a blue-green alga. The blue-green algae used in the following test examples (excluding Test Examples 1 and 2) were prepared as follows.

(1) The blue-green alga was cultured, and the culture solution was filtered to recover 1.5 L (about 1.5 g in a dry state) of the blue-green alga.

(2) The blue-green alga was washed by immersing the blue-green alga in about 4 L of tap water for 10 minutes and stirring occasionally. This washing was performed three times and water was drained using a fluororesin washing basket.

(3) The same washing as in (2) was performed three times using pure water in place of tap water.

(4) The blue-green alga was immersed in 2 L of a 7 mass % hydrochloric acid solution for 10 minutes and filtered using a stainless steel sieve. The blue-green alga was washed by immersing in about 4 L of pure water for 10 minutes and stirring occasionally.

(5) The blue-green alga was washed by immersing in about 4 L of pure water for 10 minutes and stirring occasionally. This washing was performed three times and water was drained using a stainless steel sieve.

(6) The blue-green alga was dried in air and then additionally vacuum-dried using a dry pump.

(7) The blue-green alga was crushed using Wonder Crusher WC-3L (commercially available from OSAKA CHEMICAL Co., Ltd.) to obtain a dried product of the blue-green alga in the form of powder.

<Metal Adsorption Ratio>

In the following test examples, the ratio of the metal (for example, gold) adsorbed to the blue-green alga was determined as follows. The metal solution after the immersion of the blue-green alga was filtered, and the concentration of metal element in the filtrate was measured through inductively coupled plasma mass spectrometry (ICP-MS). The adsorption ratio was calculated according to the following formula.

absorption ratio (%) =

$$\{(\text{concentration of metal element in the metal solution before adding blue-green alga}) - (\text{concentration of metal element in the filtrate})\} / (\text{concentration of metal element in the metal solution before adding blue-green alga}) \times 100$$

<Density of Gold Nanoparticles>

In the following test examples, the density of gold nanoparticles adsorbed on the surface of blue-green alga (particles/$cm^2$) was determined by counting the number of gold nanoparticles observed as white dots in an SEM image (with a magnification of 2 to 100,000) of the blue-green alga.

TABLE 1-continued

| | Element composition (at %) | | | |
|---|---|---|---|---|
| | Before HCl treatment | HCl treatment once | HCl treatment twice | HCl treatment three times |
| K2p | 0.37 | 0 | 0 | 0 |
| Si2p | 0.23 | 0 | 0 | 0 |

0.1 g of the dry blue-green alga powder was added to 500 mL of deionized water in which tetrachloroauric acid-tetrahydrate was dissolved (gold concentration: 0.57 ppm), and the blue-green alga was immersed for 1 hour (alga/Au ratio: 351) while stirring the aqueous tetrachloroauric acid solution at 500 rpm. The solution containing the blue-green alga was filtered through oiled paper, and the ratio of gold adsorbed to the blue-green alga was calculated from the gold concentration in the filtrate. The results are shown in Table 2. When the blue-green alga was treated with hydrochloric acid once or twice, the gold adsorption ratio was higher than when the blue-green alga was treated with hydrochloric acid three times.

TABLE 2

| Number of HCl treatments | Au concentration (ppm) | pH | Temperature (° C.) | Time (h) | Alga/Au ratio | Adsorption ratio (%) |
|---|---|---|---|---|---|---|
| 1 | 0.57 | 3 | RT | 1 | 351 | 85.6 |
| 2 | 0.57 | 3 | RT | 1 | 351 | 87.5 |
| 3 | 0.57 | 3 | RT | 1 | 351 | 71.9 |

<Test Example 1> Treatment of Blue-Green Alga with Hydrochloric Acid

A dry blue-green alga powder was prepared as described above. However, the treatment with hydrochloric acid and washing in (4) were performed 1 to 3 times. Elements contained in the hydrochloric acid waste solution were analyzed by ICP-MS. In addition, the element composition of the blue-green alga before and after the treatment with hydrochloric acid was analyzed through X-ray photoelectron spectroscopy (XPS).

FIG. 1 shows elements contained in the hydrochloric acid waste solution. In FIG. 1, the reference is a 7 mass % hydrochloric acid solution. 1 ppb is the detection limit of ICP-MS. As shown in FIG. 1, even after the third treatment with hydrochloric acid, elution of P, B, Cr, and Fe continued. It should be noted that P and B are elements constituting blue-green alga, and it can be considered that Cr and Fe were eluted from the stainless steel sieve used for filtration. Table 1 shows the element composition of the blue-green alga. By treating the blue-green alga with hydrochloric acid, the main constituent elements of the blue-green alga became C, N, O, P, and S only.

TABLE 1

| | Element composition (at %) | | | |
|---|---|---|---|---|
| | Before HCl treatment | HCl treatment once | HCl treatment twice | HCl treatment three times |
| C1s | 48.84 | 93.55 | 94.4 | 94.41 |
| O1s | 26.23 | 1.85 | 0.96 | 0.93 |
| Ca2p | 11.91 | 0 | 0 | 0 |
| N1s | 5.67 | 4.04 | 4.19 | 4.18 |
| P2p | 4.78 | 0.28 | 0.23 | 0.19 |
| Mg2s | 1.51 | 0 | 0 | 0 |
| S2p | 0.45 | 0.28 | 0.22 | 0.29 |

<Test Example 2> Treatment of Blue-Green Alga with Ethanol

A dry blue-green alga powder was prepared as described above. However, after the treatment with hydrochloric acid and washing in (4), a step of immersing the blue-green alga in 500 mL of ethanol for about 30 minutes was added. Components eluted into the ethanol waste solution were analyzed by obtaining an absorption spectrum of the ethanol waste solution (yellow-black color). In addition, the element composition of the blue-green alga after the ethanol treatment was analyzed by XPS.

Figure 2:
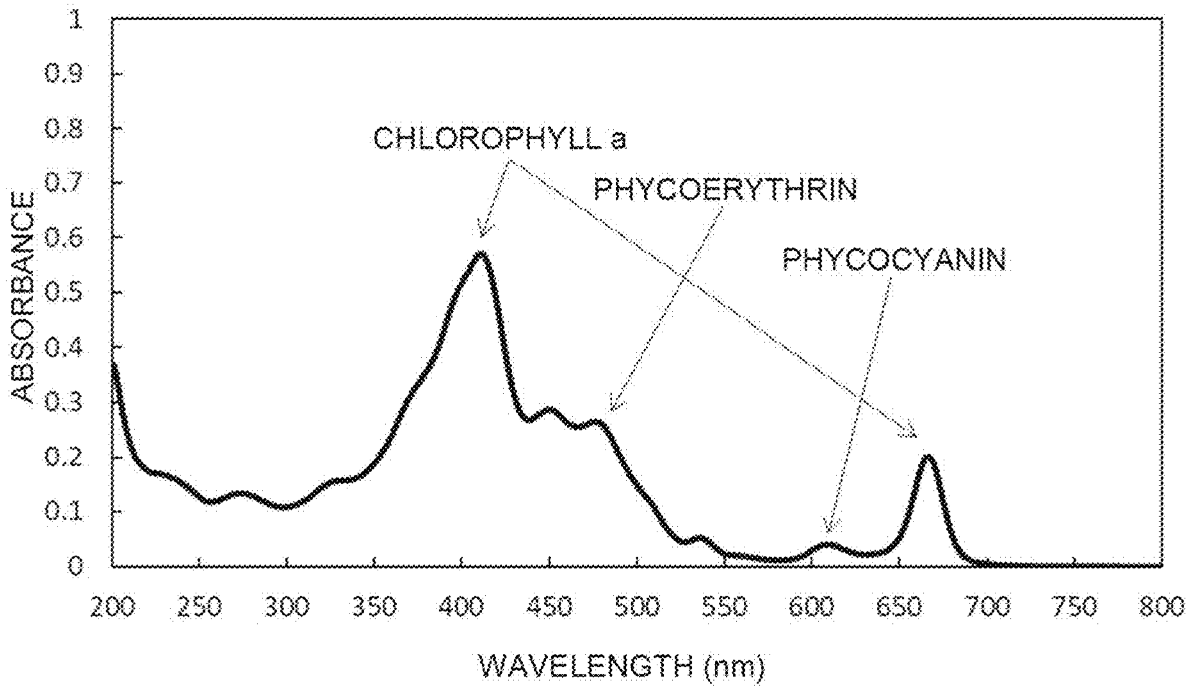
FIG. 2 shows an absorption spectrum of an ethanol waste solution produced when a blue-green alga was treated with ethanol.

FIG. 2 shows the absorption spectrum of the ethanol waste solution. It was found from the absorption spectrum that photosynthetic pigments (chlorophyll a, phycoerythrin, and phycocyanin) were eluted by the ethanol treatment. Table 3 shows element compositions of the blue-green alga after the ethanol treatment. By treating the blue-green alga with ethanol after the treatment with hydrochloric acid, P and S that remained after the treatment with hydrochloric acid disappeared and the main constituent elements of the blue-green alga became C, O, and N only.

TABLE 3

| | Element composition (at %) | | |
|---|---|---|---|
| | Before HCl treatment | After HCl treatment | After ethanol treatment |
| C1s | 48.84 | 93.55 | 63.31 |
| O1s | 26.23 | 1.85 | 32.56 |
| Ca2p | 11.91 | 0 | 0 |
| N1s | 5.67 | 4.04 | 4.13 |
| P2p | 4.78 | 0.28 | 0 |
| Mg2s | 1.51 | 0 | 0 |
| S2p | 0.45 | 0.28 | 0 |

TABLE 3-continued

| | Element composition (at %) | | |
|---|---|---|---|
| | Before HCl treatment | After HCl treatment | After ethanol treatment |
| K2p | 0.37 | 0 | 0 |
| Si2p | 0.23 | 0 | 0 |

Figure 3:
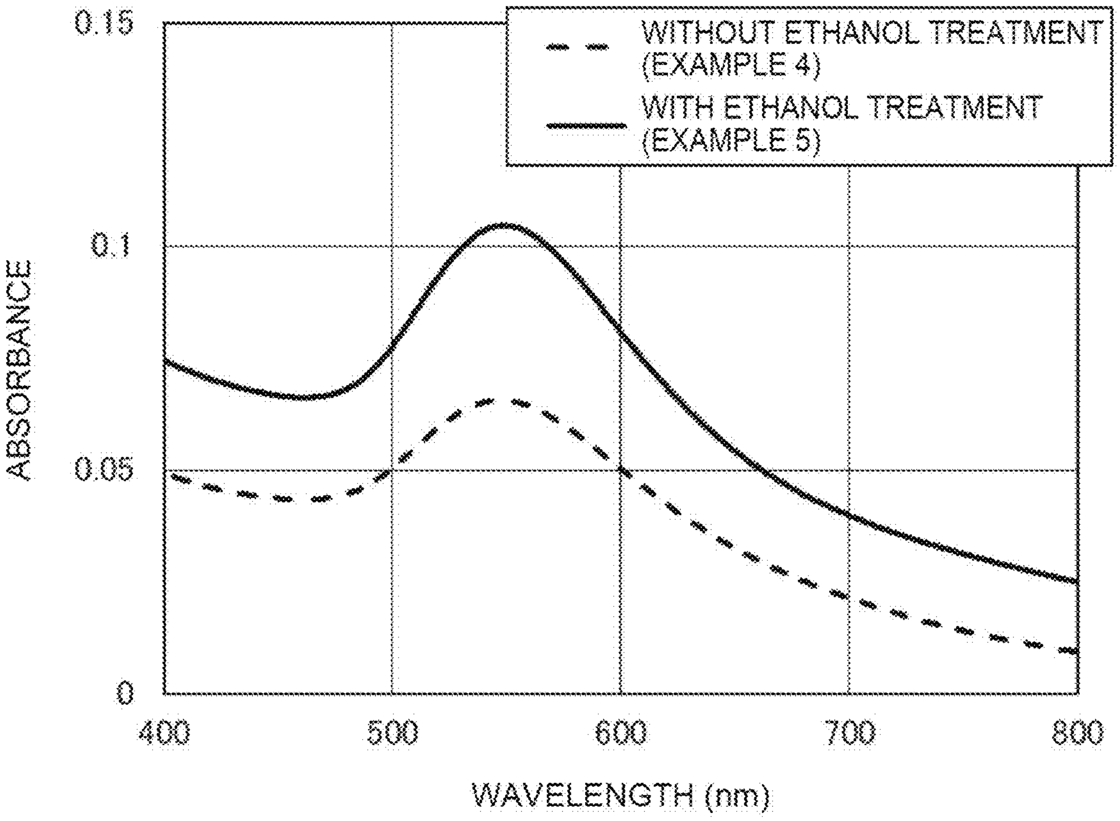
FIG. 3 shows absorption spectrums of solutions obtained by immersing a blue-green alga treated or untreated with ethanol in an aqueous tetrachloroauric acid solution.

0.3 g of the dry blue-green alga powder was added to 500 mL of deionized water in which tetrachloroauric acid-tetrahydrate was dissolved, and the blue-green alga was immersed for 3 hours while stirring the aqueous tetrachloroauric acid solution at 500 rpm or 750 rpm. A solution containing the blue-green alga was filtered through oiled paper, and the ratio of gold adsorbed to the blue-green alga was calculated from the gold concentration in the filtrate. The conditions of immersion and the adsorption ratios are shown in Table 4. In addition, the absorption spectrum of the filtrate is shown in FIG. 3. For comparison, the gold adsorption ratio and absorption spectrum were determined in the same manner using the blue-green alga that was not treated with ethanol.

TABLE 4

| Example | Ethanol treatment | Au concentration (ppm) | Alga/Au ratio | pH | Temperature (° C.) | Time (h) | Adsorption ratio (%) |
|---|---|---|---|---|---|---|---|
| 1 | — | 5.0 | 120 | 4.30 | RT | 3 | 92.6 |
| 2 | Yes | 5.0 | 120 | — | RT | 3 | 99.6 |
| 3 | Yes | 0.5 | 1200 | — | RT | 3 | 99.0 |
| 4 | — | 50 | 12 | — | 25° C. | 3 | — |
| 5 | Yes | 50 | 12 | — | RT | 3 | — |

When the blue-green alga was treated with ethanol, the gold adsorption ratios were significantly higher than when the blue-green alga was not treated with ethanol. In addition, when the blue-green alga was treated with ethanol, the absorbance at 510 to 650 nm increased by 1.7 times. This indicates that the concentration of gold nanoparticles in the filtrate was increased by 1.7 times by the treatment of the blue-green alga with ethanol.

<Test Example 3> Examination of Immersion Conditions

A dry blue-green alga powder was added to 500 mL of a metal solution, and the blue-green alga was immersed while stirring the solution at 500 rpm. Table 5 shows conditions of the immersion. The solution containing the blue-green alga was filtered through oiled paper, and the ratio of gold adsorbed to the blue-green alga was calculated from the gold concentration in the filtrate. As the metal solution, deionized water in which tetrachloroauric acid-tetrahydrate was dissolved was used in Examples 6 to 15, and hot spring water was used in Example 16. The results are also shown in Table 5.

TABLE 5

| Example | Au concentration (ppm) | Alga (g) | Alga/Au ratio | pH | Temperature (° C.) | Time (h) | Adsorption ratio (%) |
|---|---|---|---|---|---|---|---|
| 1 | 5.00 | 0.30 | 120 | 4.30 | RT | 3 | 92.6 |
| 6 | 0.53 | 0.30 | 1132 | 5.50 | RT | 3 | 84.7 |
| 7 | 0.12 | 0.30 | 5000 | 5.50 | RT | 3 | 83.3 |
| 6 | 0.53 | 0.30 | 1132 | 5.50 | RT | 3 | 84.7 |
| 8 | 0.55 | 0.011 | 40 | 5.50 | RT | 3 | 32.7 |
| 9 | 0.55 | 0.0012 | 4.4 | 5.50 | RT | 3 | 5.7 |
| 10 | 0.24 | 0.300 | 2500 | — | RT | 55 | 89.6 |
| 11 | 0.24 | 0.1230 | 1025 | — | RT | 55 | 80.0 |
| 12 | 0.24 | 0.0155 | 129 | — | RT | 55 | 50.0 |
| 13 | 0.24 | 0.0011 | 9.2 | — | RT | 55 | 8.3 |
| 14 | 0.67 | 0.30 | 896 | — | RT | 0.5 | 90.7 |
| 15 | 0.67 | 0.30 | 896 | — | RT | 1 | 96.3 |
| 6 | 0.53 | 0.30 | 1132 | 5.50 | RT | 3 | 84.7 |
| 10 | 0.24 | 0.30 | 2500 | — | RT | 55 | 89.6 |
| 16 | 0.47 | 0.30 | 1277 | 3.80 | RT | 3 | 93.0 |

Even when the concentration of gold in the aqueous tetrachloroauric acid solution was very low (0.12 ppm), an adsorption ratio of more than 80% was obtained. The larger the amount of the blue-green alga (namely, the larger the alga/Au ratio), the higher the adsorption ratio tended to be. The immersion time did not affect the adsorption ratio.

Figure 4:
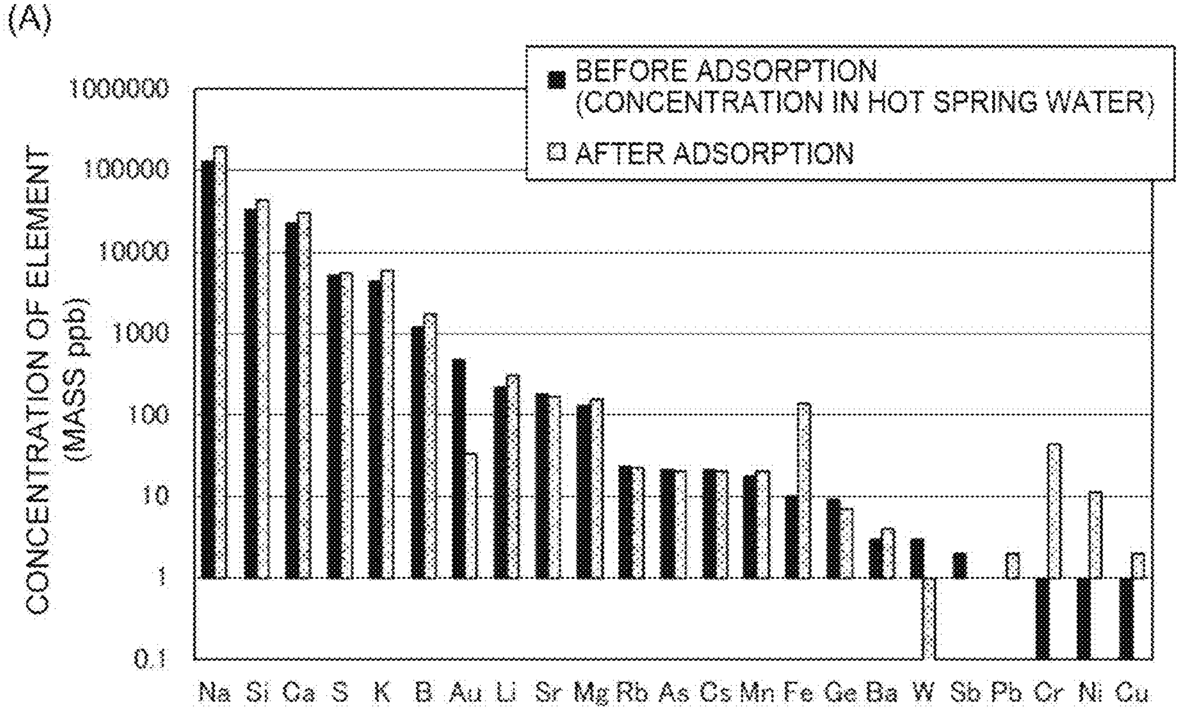
FIG. 4(A) shows concentrations of elements in a solution obtained by immersing a blue-green alga in hot spring water and FIG. 4(B) shows adsorption ratios of metals when a blue-green alga was immersed in hot spring water.
Figure 4:
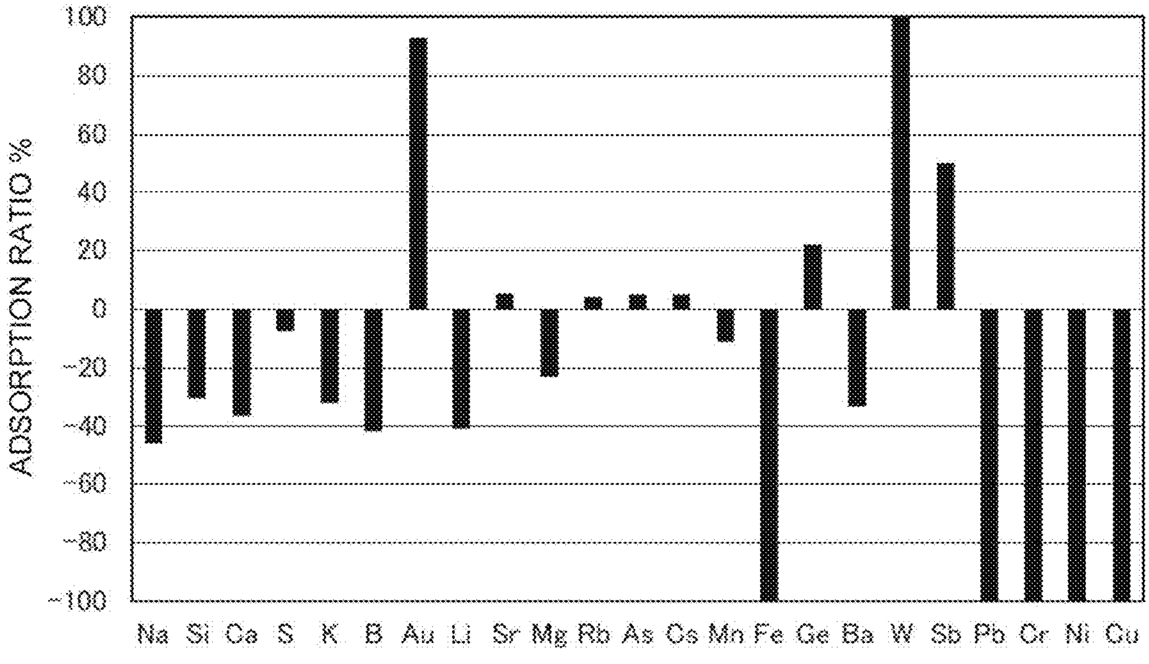

In Example 16 in which hot spring water was used as the metal solution, the concentrations of metals other than gold in the filtrate were also measured and the adsorption ratios were calculated. The results are shown in FIGS. 4(A) and 4(B). FIG. 4(A) shows the metal concentrations in the filtrate, and FIG. 4(B) shows the adsorption ratios of the metals. 1 ppb is the detection limit of ICP-MS.

<Test Example 4> Gold Nanoparticle Analysis 1

0.2 g of a dry blue-green alga powder was added to 200 mL of deionized water in which tetrachloroauric acid-tetrahydrate was dissolved, and the blue-green alga was immersed at 25° C. for 1 to 48 hours while stirring the aqueous tetrachloroauric acid solution at 500 rpm. The gold concentration in the solution was adjusted to 12.5 ppm, 25 ppm, 50 ppm, 125 ppm, 250 ppm, 500 ppm, 1,000 ppm, 2,500 ppm, 5,000 ppm, or 10,000 ppm. The solution containing the blue-green alga was filtered using oiled paper, filter paper (1.6 μm), and filter paper (0.7 μm) in this order, and the blue-green alga was dried. The surface of the blue-green alga was observed under an SEM, and the density of gold nanoparticles adsorbed on the surface of the blue-green alga was measured. The results are shown in FIGS. 5(A) and 5(B).

Figure 5:
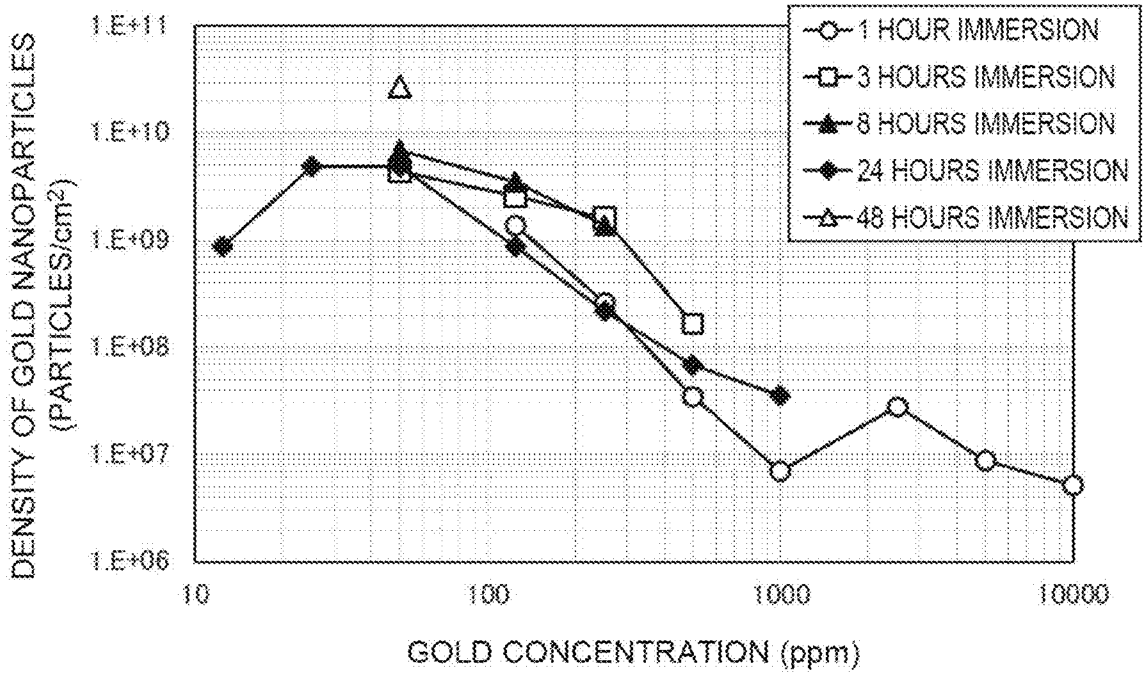
FIG. 5(A) shows the relationship between the gold concentration in an aqueous tetrachloroauric acid solution and the density of gold nanoparticles adsorbed on the surface of a blue-green alga and FIG. 5(B) shows SEM images of the surface of a blue-green alga immersed in an aqueous tetrachloroauric acid solution for 24 hours.
Figure 5:
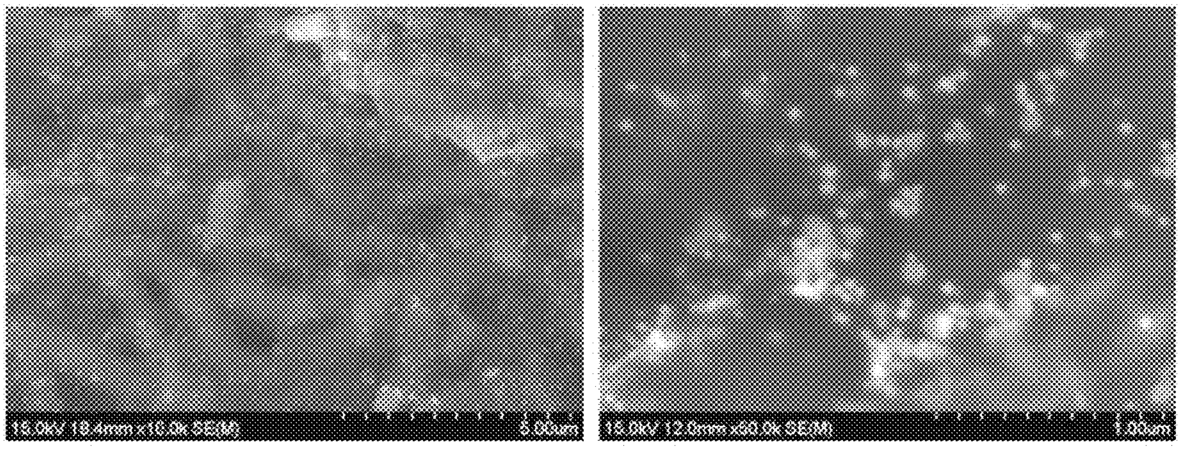

FIG. 5(A) shows the relationship between the gold concentration in an aqueous tetrachloroauric acid solution and the density of gold nanoparticles adsorbed on the surface of the blue-green alga. At gold concentrations of 50 ppm or more, it was shown that, the lower the gold concentration (namely, the higher the alga/Au ratio), the higher the density of gold nanoparticles adsorbed on the surface of the blue-green alga. For immersion times of 8 hours or shorter, there was a tendency for the density of gold nanoparticles adsorbed on the surface of the blue-green alga to increase as the immersion time increased. FIG. 5(B) shows SEM images of the surface of the blue-green alga immersed in an aqueous tetrachloroauric acid solution (gold concentration: 25 ppm) for 24 hours. The left image in FIG. 5(B) is an image with a magnification of 10,000, and the right image is an image with a magnification of 50,000. From these images, it is clear that the nanoparticles are adsorbed on the surface of the blue-green alga. In addition, it was confirmed that the nanoparticles adsorbed on the surface of the blue-green alga were gold single crystals according to analysis using a transmission electron microscope (TEM) and X-ray diffraction (XRD).

<Test Example 5> Gold Nanoparticle Analysis 2

0.2 g of a dry blue-green alga powder was added to 200 mL of deionized water in which tetrachloroauric acid-tetrahydrate was dissolved (gold concentration: 50 ppm), and the blue-green alga was immersed at 50° C. or 75° C. for 24 hours while stirring the aqueous tetrachloroauric acid solution at 500 rpm. The solution containing the blue-green alga was filtered using oiled paper, filter paper (1.6 μm), and filter paper (0.7 μm) in this order, and the blue-green alga was dried. The surface of the blue-green alga was observed under an SEM, and the density of gold nanoparticles adsorbed on the surface of the blue-green alga was measured. The filtrate was recovered, and the absorbance thereof was measured.

Table 6 shows the density of gold nanoparticles adsorbed on the surface of the blue-green alga. For comparison, the density of gold nanoparticles in Test Example 4 in which the blue-green alga was immersed at 25° C. is also shown in Table 6. When the temperature during the immersion was 50° C. or 75° C., the density of nanoparticles increased to about twice that when the temperature during immersion was 25° C.

TABLE 6

| Au concentration (ppm) | Alga/Au ratio | pH | Temperature (° C.) | Time (h) | Density of gold nanoparticles (particles/cm$^2$) |
|---|---|---|---|---|---|
| 50 | 20 | 3 | 25 | 24 | $4.9 \times 10^9$ |
| 50 | 20 | 3 | 50 | 24 | $1.3 \times 10^{10}$ |
| 50 | 20 | 3 | 75 | 24 | $9.7 \times 10^9$ |

Figure 6:
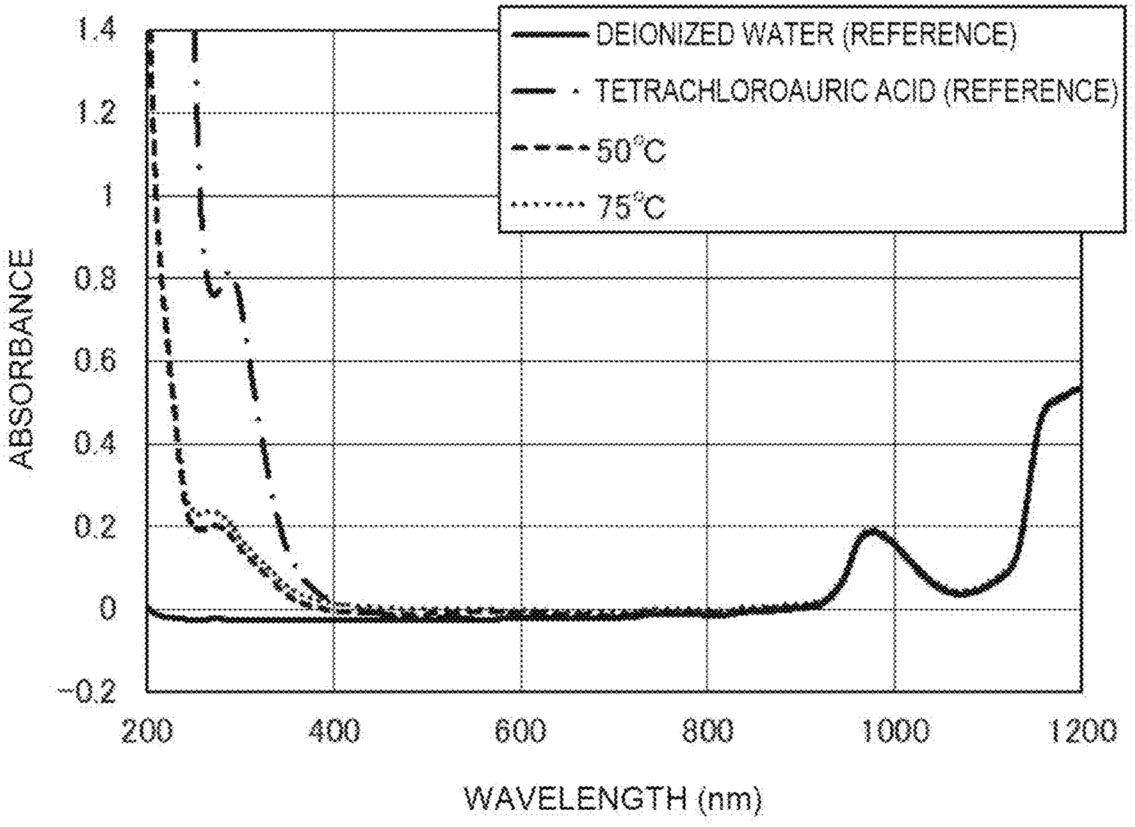
FIG. 6 shows absorption spectrums of solutions obtained by immersing a blue-green alga in an aqueous tetrachloroauric acid solution at 50° C. or 75° C.

FIG. 6 shows the absorption spectrum of the filtrate. When the temperature during immersion was 50° C. or 75° C., the filtrate was transparent, and no absorption was observed at 510 to 650 nm, and thus, it was found that the filtrate contained almost no gold nanoparticles. Meanwhile, when the temperature during immersion was 25° C., the filtrate exhibited a red color specific to gold nanoparticles, which suggested that gold nanoparticles were present in the filtrate.

<Test Example 6> Gold Nanoparticle Analysis 3

Figure 7:
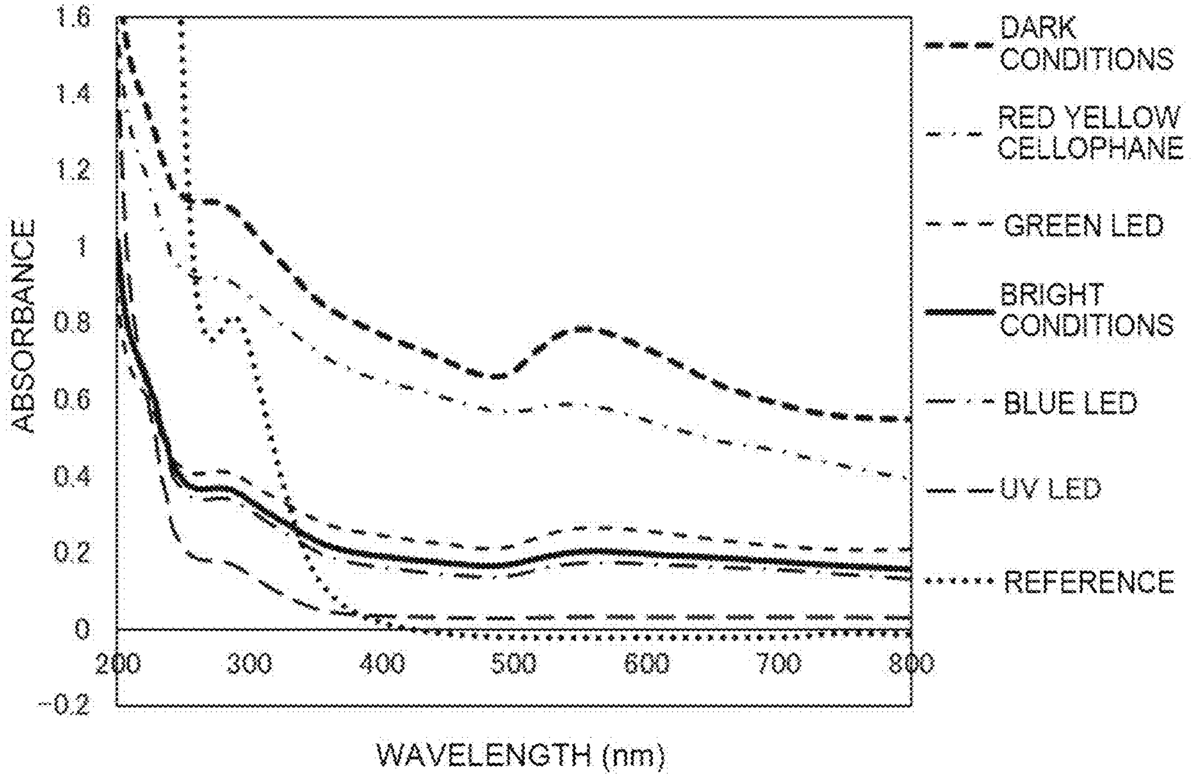
FIG. 7 shows absorption spectrums of solutions obtained by immersing a blue-green alga in an aqueous tetrachloroauric acid solution while applying light beams of different wavelengths.

0.3 g of a dry blue-green alga powder was put into a beaker containing 200 mL of deionized water in which tetrachloroauric acid-tetrahydrate was dissolved (gold concentration: 100 ppm), and the blue-green alga was immersed under indoor lighting with a white LED (435 to 800 nm) at 30° C. for 3 days, while stirring the aqueous tetrachloroauric acid solution at 300 rpm. The solution containing the blue-green alga was filtered, and the absorbance of the filtrate was measured. The same experiment was performed while irradiating with ultraviolet light (UV) LED (350 to 400 nm, irradiation intensity: 150 mW (radiant flux intensity unit)), blue LED (435 to 490 nm, irradiation intensity: 200 mW (radiant flux intensity unit)), or green LED (495 to 545 nm, irradiation intensity: 200 mW (radiant flux intensity unit)), or while covering the entire beaker with a red yellow cellophane (which absorbs light of 600 nm or less; and the inside of the beaker was irradiated with light of 600 to 800 nm, and 100 mW (radiant flux intensity unit)). In addition, the same experiment was performed while blocking the beaker from light by covering the entire beaker with an aluminum foil. FIG. 7 shows the absorbances of the filtrates.

In FIG. 7, the reference is an aqueous tetrachloroauric acid solution before the blue-green alga was immersed. As shown in FIG. 7, when the solution was blocked from light using an aluminum foil (dark conditions), the absorbance at 510 to 650 nm was higher than when the solution was not blocked from light (bright conditions). In addition, the higher the energy of the light with which the solution was irradiated, the lower the absorbance at 510 to 650 nm became. From these results, it was found that, under dark conditions in which light is blocked, the produced gold nanoparticles tend to be released from the blue-green alga into the solution, while when the solution is irradiated with light, the release of the produced gold nanoparticles from the blue-green alga is reduced and more gold nanoparticles remain adsorbed to the blue-green alga. In addition, it was also found that, the higher the energy of the light with which the solution is irradiated, the more the release of gold nanoparticles is reduced and the amount of gold nanoparticles adsorbed to the blue-green alga increases.

<Test Example 7> Gold Nanoparticle Analysis 4

0.2 g of a dry blue-green alga powder was added to 200 mL of deionized water in which tetrachloroauric acid-tetrahydrate was dissolved (gold concentration: 50 ppm or 200 ppm), and the blue-green alga was immersed at 25° C. for 24 hours while stirring the aqueous tetrachloroauric acid solution at 500 rpm. The solution containing the blue-green alga was filtered using oiled paper, filter paper (1.6 μm), and filter paper (0.7 μm) in this order. The filtrate was recovered and gold nanoparticles in the filtrate were observed under a TEM.

Figure 8:
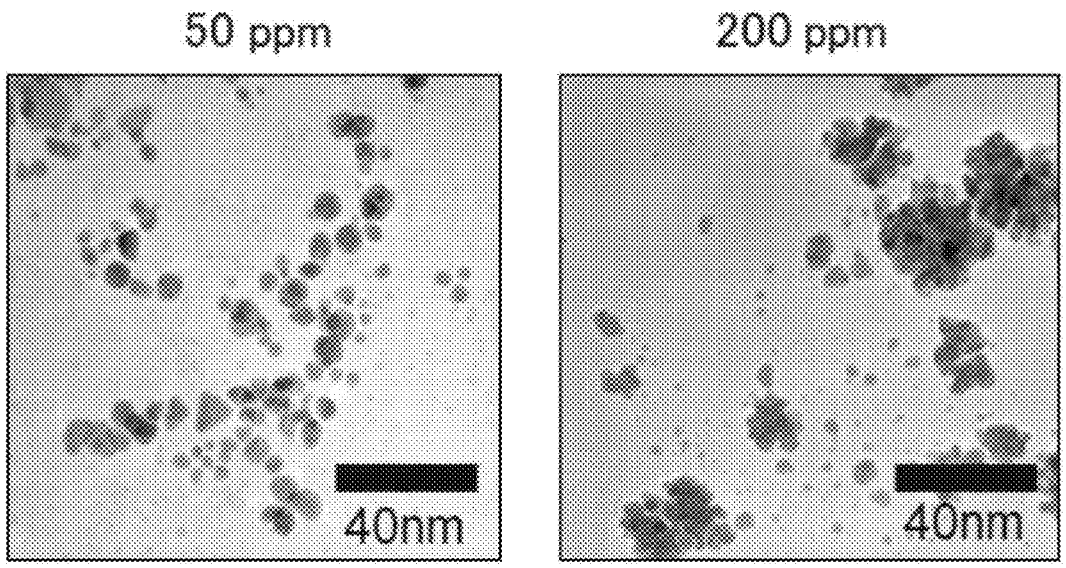
FIG. 8 shows TEM images of gold nanoparticles in solutions obtained when a blue-green alga was immersed in an aqueous tetrachloroauric acid solution (gold concentration: 50 ppm or 200 ppm).

FIG. 8 shows TEM images. The left image in FIG. 8 shows gold nanoparticles obtained from an aqueous tetrachloroauric acid solution containing 50 ppm of gold, and the right image shows gold nanoparticles obtained from an aqueous tetrachloroauric acid solution containing 200 ppm of gold. Some of the gold nanoparticles aggregated when the gold concentration was 200 ppm, whereas the gold nanoparticles did not aggregate when the gold concentration was 50 ppm and a colloidal gold solution in which gold nanoparticles were dispersed was obtained.

The zeta potential of gold nanoparticles in a colloidal gold solution obtained from an aqueous tetrachloroauric acid solution with a gold concentration of 50 ppm was measured by dynamic light scattering (DLS). The zeta potential was-20 mV, which indicates that the gold nanoparticles can be stably dispersed in the solution.

<Test Example 8> Gold Nanoparticle Analysis 5

Various analyses were performed on the colloidal gold solution obtained from the aqueous tetrachloroauric acid solution with a gold concentration of 50 ppm in Test Example 7, in order to elucidate the surface conditions of the gold nanoparticles.

First, the average particle size of gold nanoparticles in a colloidal gold solution was determined by dynamic light scattering (DLS) and by measuring the absorbance at 510 to 650 nm. The average particle size measured by DLS was 105 nm. On the other hand, the average particle size calculated from the maximum absorption wavelength of the colloidal gold solution was about 90 nm. The particle size determined by DLS corresponds to the Stokes radius (that is, the particle size assuming that the entire structure involved in the reaction is a particle), whereas the particle size calculated from the absorbance is the particle size of the gold nanoparticle itself. Therefore, the difference (15 nm) in these average particle sizes is presumed to be the size of the surface modification structure of the gold nanoparticles.

Figure 9:
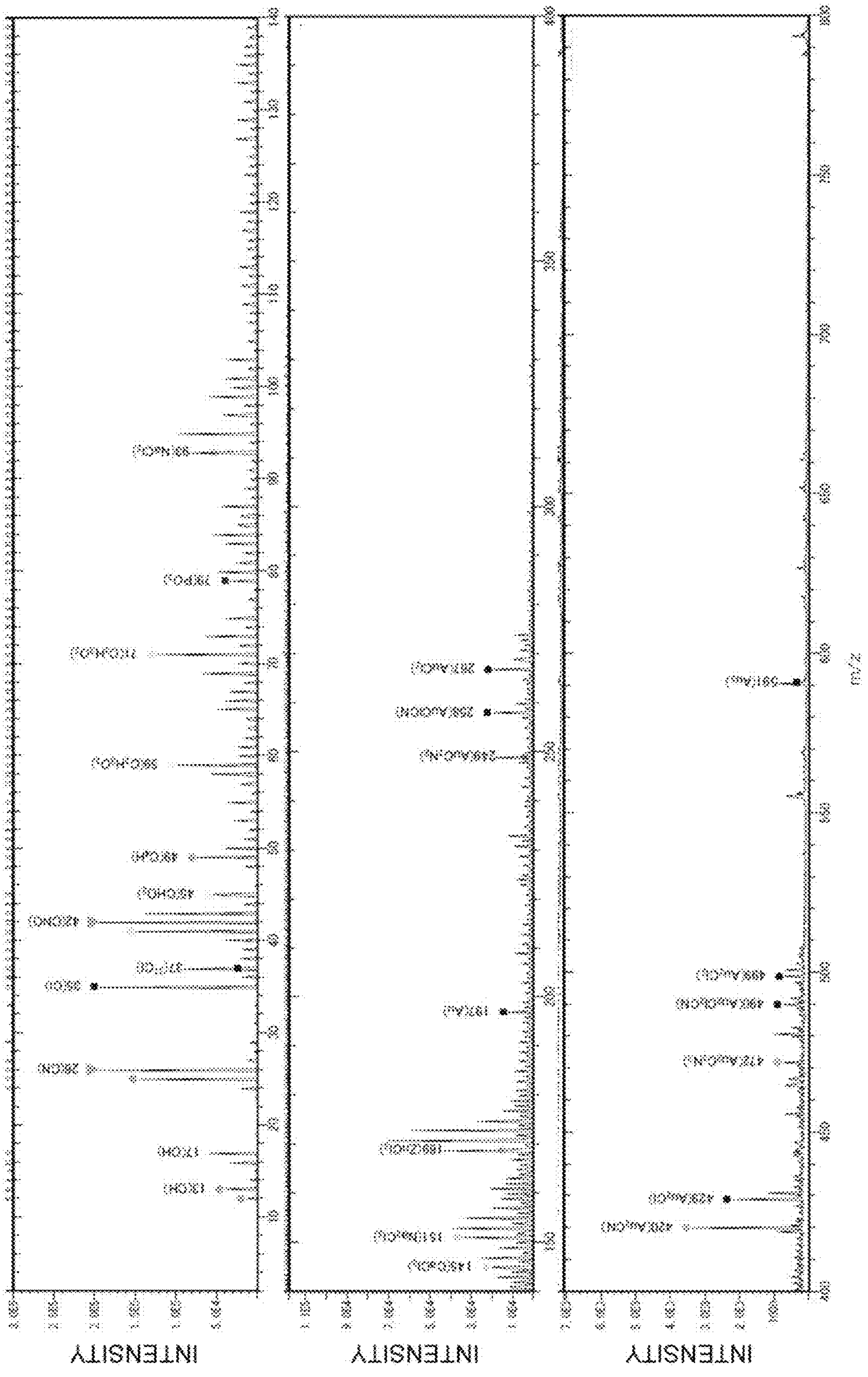
FIG. 9 shows TOF-SIMS results of a colloidal gold solution.

Next, molecule species present in the colloidal gold solution were analyzed through time-of-flight secondary ion mass spectrometry (TOF-SIMS). An analysis sample was prepared by applying and drying a total of 3 mL of a colloidal gold solution to an area with a diameter of about 10 mm on a clean Si substrate (10 mm×10 mm) while heating on a hot plate at 100° C. The TOF-SIMS results are shown in FIG. 9. $AuC_2N_2$ and $Au_2C_3N_3$ were significantly observed. In addition, fragments such as CN, CNO, and COOH were confirmed. These results strongly suggest that an AuCN-based compound is present in the gold nanoparticles.

Figure 10:
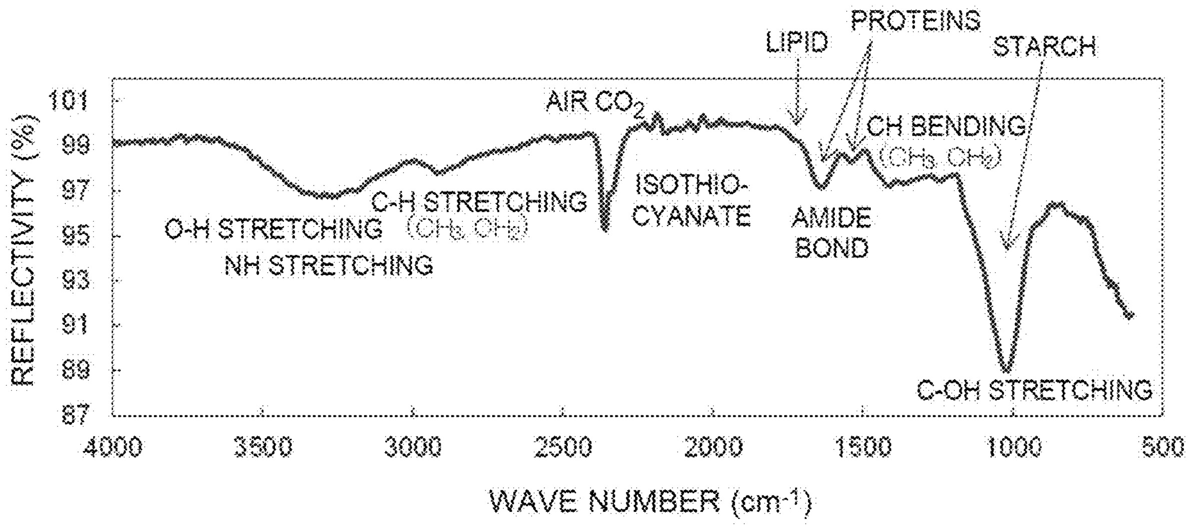
FIG. 10 shows FT-IR results of a colloidal gold solution.

Next, molecule species present in the colloidal gold solution were analyzed by Fourier-transform infrared spectroscopy (FT-IR) using attenuated total reflection (ATR). An analysis sample was prepared by applying and drying the colloidal gold solution to a Si substrate in the same manner as above, and then scraping off the dried product and inserting it between crystals. The FT-IR results are shown in FIG. 10. It was found that the colloidal solution had amide bonds, proteins, and starch. In addition, C—H—O bonds were also observed.

From the above results, it was found that gold nanoparticles have a surface modification with a size of 10 to 50 nm, which is an AuCN-based molecule containing C, O, N, and H as main components and having an amide bond. From these features, a protein formed by binding a plurality of amino acids is likely to be the presumed surface modification of the gold nanoparticles.

<Test Example 9> Isolation of Gold Nanoparticles 0.2 g of a dry blue-green alga powder was added to 200 mL of deionized water in which tetrachloroauric acid-tetrahydrate was dissolved (gold concentration: 50 ppm), and the blue-green alga was immersed at 25° C. for 3 hours while stirring the aqueous tetrachloroauric acid solution at 500 rpm. The solution containing the blue-green alga was filtered using oiled paper, filter paper (1.6 μm), and filter paper (0.7 μm) in this order. The filtrate (colloidal gold solution) was recovered, and the absorbance thereof was measured. The blue-green alga was suspended in 200 mL of deionized water and ultrasonicated at 25° C. and 38 kHz for 1 hour. The solution after the ultrasonication was filtered using a filter paper (0.7 μm) and the absorbance of the filtrate was measured. In addition, the surface of the blue-green alga before and after the ultrasonication was observed under an SEM, and the density of the gold nanoparticles adsorbed on the surface of the blue-green alga was measured.

Figure 11:
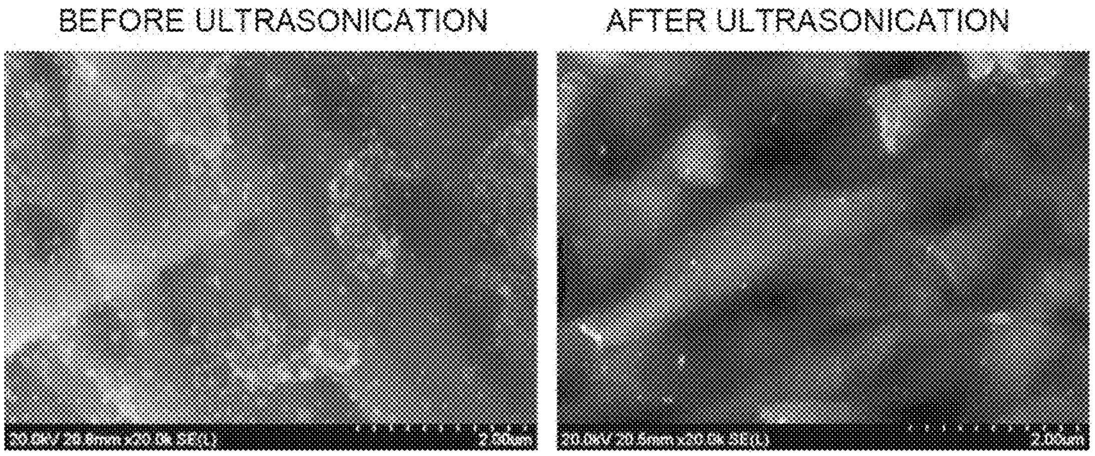
FIG. 11(A) shows SEM images of the surface of a blue-green alga before and after an ultrasonication.
FIG. 11(B) shows absorption spectrums of a solution obtained by immersing a blue-green alga in an aqueous tetrachloroauric acid solution and a solution obtained by ultrasonicating a suspension of the blue-green alga.
Figure 11:
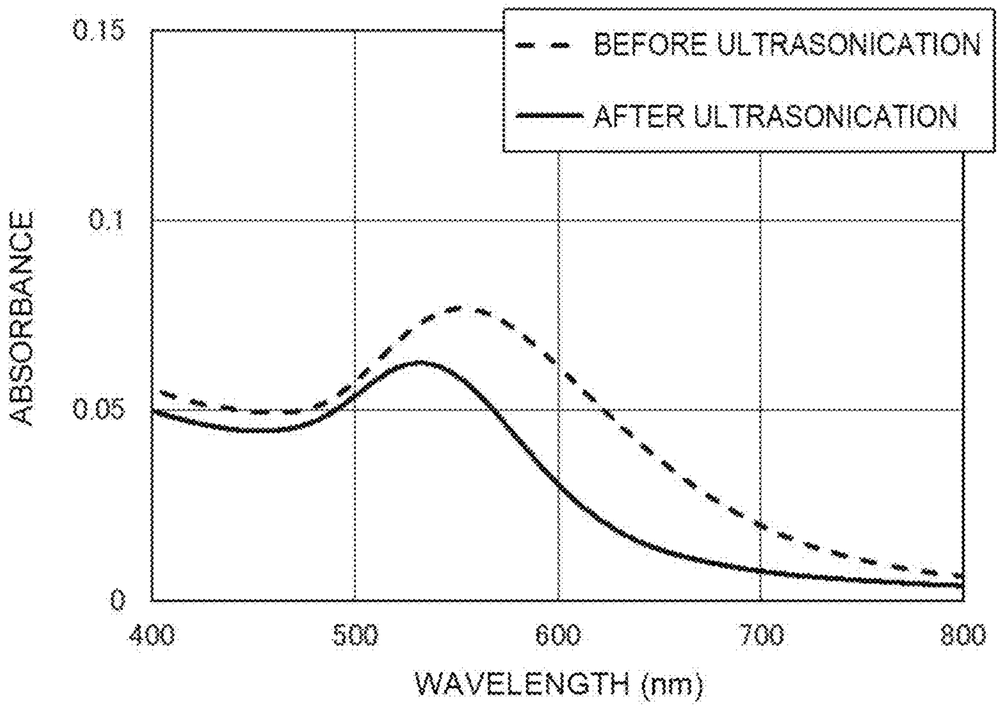

FIG. 11(A) shows SEM images of the surface of the blue-green alga. The left image in FIG. 11(A) shows the surface of the blue-green alga before the ultrasonication, and the right image shows the surface of the blue-green alga after the ultrasonication. The density of the gold nanoparticles adsorbed to the blue-green alga before the ultrasonication was $4\times10^9$ particles/cm$^2$, and the density of the gold nanoparticles adsorbed to the blue-green alga after the ultrasonication was $1\times10^9$ particles/cm$^2$.

FIG. 11(B) shows the absorption spectrum of the filtrate. The absorption at 510 to 650 nm derived from the gold nanoparticles was observed in the filtrate both before and after the blue-green alga was ultrasonicated. It should be noted that the colloidal gold solution obtained by the ultrasonication of the blue-green alga was redder than the colloidal gold solution recovered before the ultrasonication, and the absorption wavelength thereof was shorter. This indicates that the particle size of the gold nanoparticles in the colloidal gold solution obtained by the ultrasonication of the blue-green alga was smaller.

As shown by these results, by ultrasonicating the blue-green alga, about 70% of the gold nanoparticles adsorbed to the blue-green alga were able to be recovered as a colloidal gold solution.

<Test Example 10> Classification of Gold Nanoparticles 0.3 g of a dry blue-green alga powder was added to 200 mL of deionized water in which tetrachloroauric acid-tetrahydrate was dissolved (gold concentration: 50 ppm), and the blue-green alga was immersed at 25° C. for 3 hours while stirring the aqueous tetrachloroauric acid solution at 500 rpm. The solution containing the blue-green alga was filtered using oiled paper, filter paper (1.6 μm), and filter paper (0.7 μm) in this order. The filtrate (colloidal gold solution) was recovered in a 1.5 mL centrifuge tube and centrifuged at 2,500×g for 30 minutes.

Figure 12:
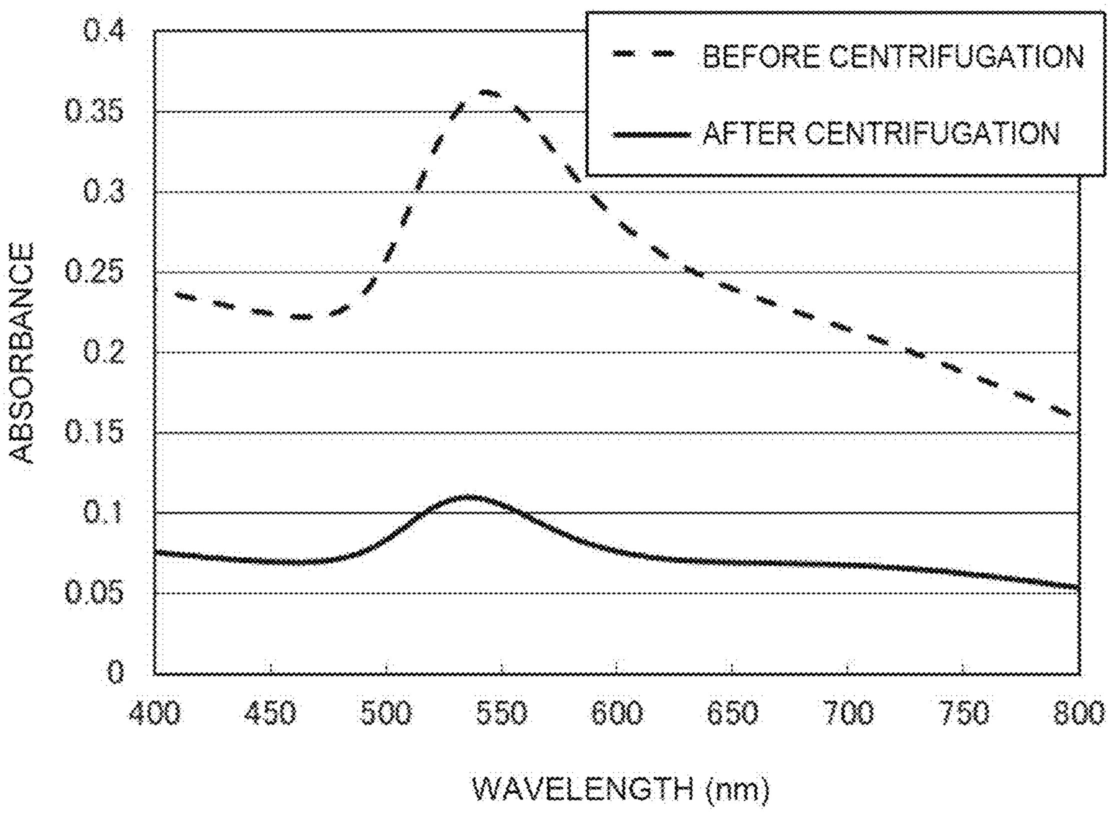
FIG. 12 shows absorption spectrums of a colloidal gold solution before and after centrifugation at 2,500×g for 30 minutes.

FIG. 12 shows the absorption spectrums of the colloidal solution before centrifugation and of the supernatant after centrifugation. The larger particles precipitated by the centrifugation, and the median particle size in the colloidal solution changed from 70 nm (corresponding to the absorption at 544 nm) to 55 nm (corresponding to the absorption at 535 nm). The above results indicate that the particle sizes of the gold nanoparticles in the colloidal gold solution can be made uniform by centrifugation.

<Test Example 11> Recovery of Gold 5.0 g of a dry blue-green alga powder was added to 1 L of deionized water in which tetrachloroauric acid-tetrahydrate was dissolved (gold concentration: 5,000 ppm, absolute amount of gold: 5.0 g, pH: 2.5), and the blue-green alga was immersed for 3 hours (alga/Au ratio: 1) while stirring the aqueous tetrachloroauric acid solution. The solution containing the blue-green alga was filtered through an oiled paper, and the blue-green alga was naturally dried for one day or longer. The dried blue-green alga was put into a SiC crucible and heated in air using an electric furnace at 800° C. for 1 hour and at 1,000° C. for 1 hour.

After heating, when the crucible was returned to room temperature, 0.39 g of yellow granular gold was obtained. The yield based on the initial mass of gold was about 8%, which was a high recovery ratio. Gold with a purity of 3 N (99.9% or more) is dull reddish-brown, but gold with a purity of 4 N (99.99% or more) or more is golden yellow. Therefore, it was found that the recovered gold had an extremely high purity, based on its color. In addition, when the element composition of the obtained gold was analyzed by XPS, more than 99.9% was Au, and P and O were contained at less than 0.1%. Since phosphorus contained in the blue-green alga is not easily volatilized, the detected P is thought to be derived from the blue-green alga. As shown in Test Example 2, by treating the blue-green alga with ethanol after the treatment with hydrochloric acid, phosphorus contained in the blue-green alga can be removed, and thus, it is expected that gold of higher purity can be obtained by using the blue-green alga treated with ethanol.

Figure 13:
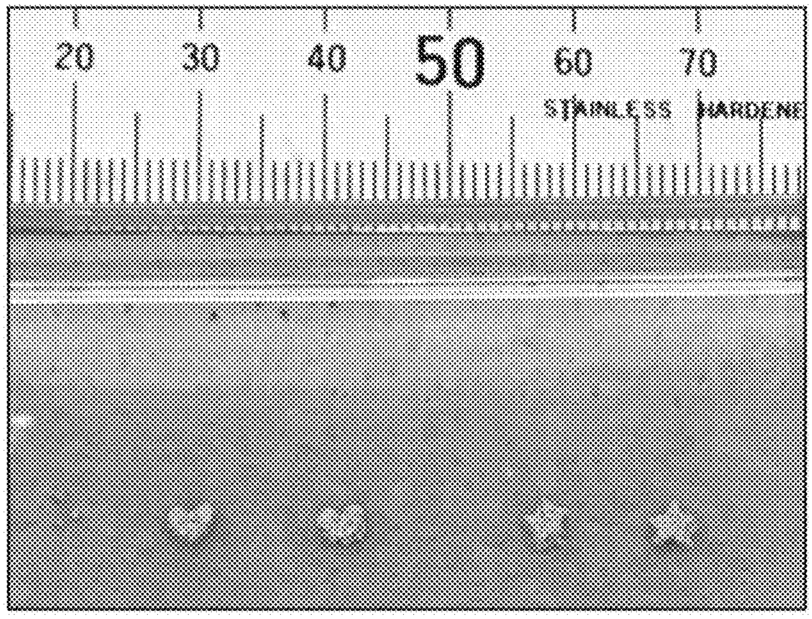
FIG. 13 shows a photo of star-shaped and heart-shaped golds.

<Test Example 12> Production of Gold Molded Product 2.5 g of a dry blue-green alga powder was added to 500 mL of deionized water in which tetrachloroauric acid-tetrahydrate was dissolved (gold concentration: 2,000 ppm), and the blue-green alga was immersed at 25° C. for 3 hours while stirring the aqueous tetrachloroauric acid solution at 500 rpm. The solution containing the blue-green alga was filtered through an oiled paper, and the blue-green alga was washed with water and then preliminarily dried for 5 minutes using a hair dryer. The blue-green alga was molded using star-shaped and heart-shaped molds and naturally dried for one day. The dried blue-green alga was put into a SiC crucible, and heated in air using an electric furnace at 800° C. for 1 hour and at 1,000° C. for 1 hour. After heating, the crucible was returned to room temperature. As shown in FIG. 13, star-shaped and heart-shaped golds were able to be obtained.

<Test Example 13> Recovery of Metals from Urban Mines 0.12 g of gold wires (metal source) was added to 400 mL of artificial seawater (salt concentration: 3.8 mass %) containing 3 mass % of nitric acid and was stirred at 200° C. and 500 rpm for 20 hours to dissolve the gold wires. 3 g of a dry blue-green alga powder was added to the obtained gold solution, and the blue-green alga was immersed for 3 hours while stirring the gold solution. The solution containing the blue-green alga was filtered through an oiled paper, and the blue-green alga was dried. The dried blue-green alga was fired at 800° C. for 1 hour and at 1,000° C. for 1 hour. The element composition of the firing residue was analyzed by XPS, and the gold recovery ratio was calculated according to the following formula.

gold recovery ratio (%)=(mass of the firing residue)×(proportion of gold in the firing residue)/(mass of gold contained in the metal source)

The same experiment was performed using 19.9 g of electronic boards containing gold plating (estimated total metal amount: 0.4 g, estimated gold amount: 0.02 g) in place of gold wires as a metal source, and the gold recovery ratio was calculated. The results are shown in Table 7, together with the conditions of the metal dissolution and conditions of the immersion of the blue-green alga.

TABLE 7

| | Example17 | Example18 |
|---|---|---|
| Metal source | Gold wire | Electronic board |
| Nitric acid concentration (mass %) | 3 | 3 |
| Salt concentration (mass %) | 3.8 | 3.8 |
| Dissolution temperature | 200 | 200 |
| Dissolution time | 20 | 20 |
| Au concentration (ppm) | 300 | 50 |
| Au concentration (mass %) | 0.03 | 0.005 |
| Alga/Au ratio | 25 | 50 |
| pH | — | 2.6 |
| Immersion temperature (° C.) | RT | RT |
| Immersion time (h) | 3 | 3 |
| Au recovery ratio (%) | 27 | 35.4 |
| Recovered metal | Au | Au, Ag, Sn, Cu, Co |

Gold was able to be recovered when either gold wires or electronic boards were used as the metal source. When electronic boards were used as the metal source, silver, tin, copper, and cobalt were also able to be recovered in addition to gold. In Example 17, the gold wires were dissolved even when seawater from Negishi Bay was used in place of artificial seawater.

Figure 14:
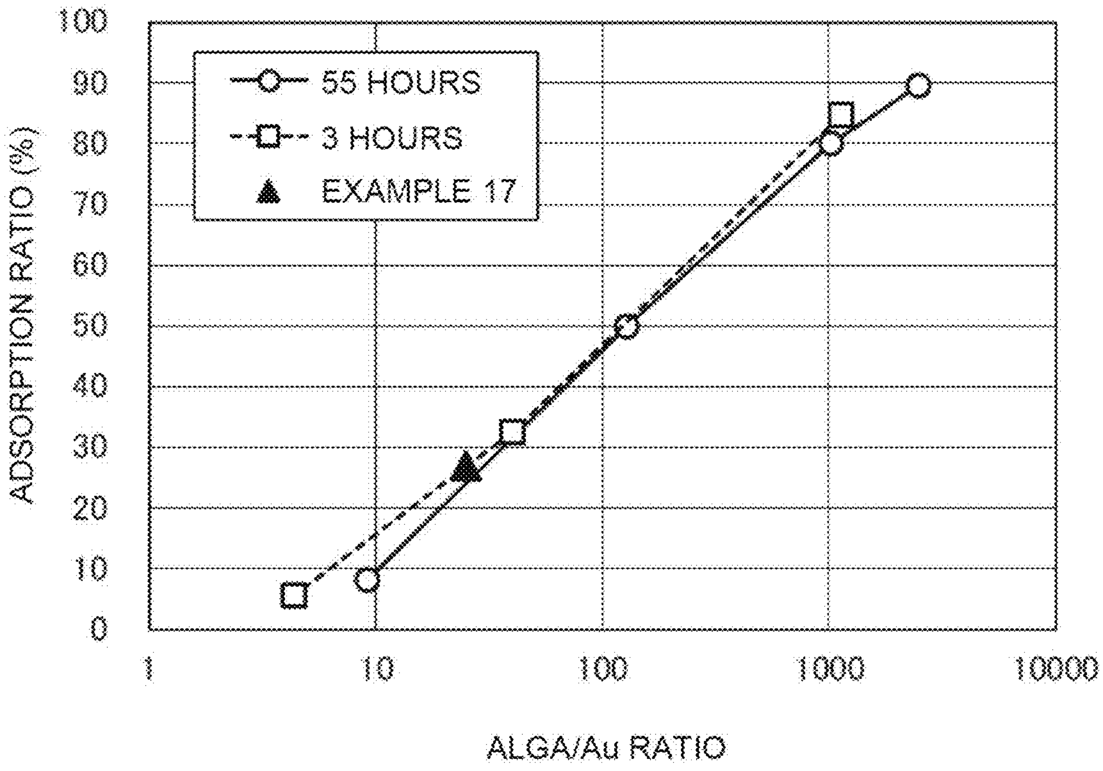
FIG. 14 shows the relationship between the alga/Au ratio and the ratio of gold adsorbed to the blue-green alga.

The gold recovery ratio in Example 17 was plotted on the graph shown in FIG. 14, together with the ratio of gold adsorbed to the blue-green alga in Examples 6, and 8 to 13 of Test Example 3 in which the blue-green alga was immersed in an aqueous tetrachloroauric acid solution. In FIG. 14, the gold recovery ratio when the blue-green alga was immersed in a gold solution obtained by dissolving gold wires was almost the same as the gold adsorption ratio when the blue-green alga was immersed in an aqueous tetrachloroauric acid solution.

Here, the utilization efficiency of the blue-green alga is considered. As shown in FIG. 14, when the alga/Au ratio is 50, the gold adsorption ratio is about 35%. At this alga/Au ratio, in order to achieve a recovery ratio of 80% or more using a metal solution containing 0.02 g of gold, it is estimated that the operations of adsorbing the gold to the blue-green alga and recovering the adsorbed gold need to be performed four times, as shown in Table 8. The total amount of the blue-green alga required in this case is about 2.35 g. On the other hand, in order to achieve a yield of 80% or more by a single adsorption and recovery operation using the same metal solution, an estimated 800 g of the blue-green alga would be required. Therefore, from the perspective of the utilization efficiency of the blue-green alga, it is preferable to recover gold in multiple stages at a low alga/Au ratio, rather than recovering gold all at once at a high alga/Au ratio.

TABLE 8

| | 1st time | 2nd time | 3rd time | 4th time |
|---|---|---|---|---|
| Alga/Au ratio | 50 | 50 | 50 | 50 |
| Gold (g) | 0.02 | 0.013 | 0.00845 | 0.00549 |
| Amount of blue-green alga (g) | 1.0 | 0.65 | 0.423 | 0.275 |
| Recovery ratio (%) | 35 | 35 | 35 | 35 |
| Amount recovered (g) | 0.0070 | 0.00455 | 0.00296 | 0.00192 |
| Total amount recovered (g) | 0.0070 | 0.0116 | 0.0145 | 0.0164 |
| Total amount of blue-green alga (g) | 1.0 | 1.65 | 2.07 | 2.35 |
| Total recovery ratio (%) | 35.0 | 57.8 | 72.5 | 82.1 |

From the above results, at various alga/Au ratios, the gold recovery ratio per single adsorption and recovery operation, the number of adsorption and recovery operations required to recover 80% of gold, and the amount of the blue-green alga required to recover 80% of gold when the solution contains 1 g of gold were calculated. The results are shown in Table 9.

TABLE 9

| Alga/Au ratio | Recovery ratio per operation (%) | Number of operations required for 80% recovery | Amount of blue-green alga required to recover 80% of 1 g of gold (g) |
|---|---|---|---|
| 3 | 5 | 30 | 47 |
| 5 | 10 | 16 | 41 |
| 20 | 20 | 8 | 83 |
| 40 | 30 | 5 | 111 |
| 70 | 40 | 4 | 152 |
| 100 | 50 | 3 | 175 |
| 250 | 60 | 2 | 350 |
| 400 | 70 | 2 | 520 |
| 800 | 80 | 1 | 800 |
| 1100 | 90 | 1 | 1100 |

<Test Example 14> Examination of Gold Dissolution Conditions 1

1 g of electronic boards containing gold wires (estimated total metal amount: 0.02 g) was added to 100 mL of artificial seawater (salt concentration: 3.80 mass %) containing 0 to 50 mass % of nitric acid and was stirred at 200° C. and 300 rpm until the gold wires were completely dissolved. 0.2 g of a dry blue-green alga powder was added to the obtained metal solution, and the blue-green alga was immersed for 3 hours while stirring the metal solution at 300 rpm. The solution containing the blue-green alga was filtered through an oiled paper, and the blue-green alga was dried. The mass of the dried blue-green alga was measured, and the residual ratio of blue-green alga was calculated according to the following formula.

$$\text{residual ratio of blue-green alga (\%)} = (\text{dry mass of the blue-green alga recovered from the metal solution}) \div (\text{mass of the blue-green alga added to the metal solution}) \times 100$$

Table 10 shows the concentration of nitric acid in the artificial seawater, the time taken to melt gold wires, and the residual ratio of blue-green alga.

TABLE 10

| Nitric acid concentration (mass %) | Nitric acid/ metal ratio | pH | Dissolution time (h) | Residual ratio (%) of blue-green alga |
|---|---|---|---|---|
| 0 | — | — | — | 100 |
| 2 | 100 | — | 48 | — |
| 3 | 150 | 2.6 | 20 | 95 |
| 10 | 500 | 2.0 | 2 | 79 |
| 20 | 1000 | 1.7 | 1 | 56 |
| 30 | 1500 | 1.5 | 1 | 39 |
| 40 | 2000 | 1.3 | 1 | 27 |
| 50 | 2500 | 1.1 | 1 | 15 |

When the concentration of nitric acid in the artificial seawater was 2 mass % or more, the gold wires were able to be completely dissolved. When the nitric acid concentration was 20 mass % or less, the higher the nitric acid concentration, the shorter the time required to dissolve the gold wires. On the other hand, as the concentration of nitric acid became higher, the blue-green alga became more easily dissolved and the residual ratio of the blue-green alga after immersion decreased.

<Test Example 15> Examination of Gold Dissolution Conditions 2

1 g of electronic boards containing gold wires (estimated total metal amount: 0.02 g) was added to 100 mL of a solution containing 10 mass % of nitric acid and 0.1 to 20 mass % of salts (Marine Art SF-1 (commercially available from Osaka Yakken Co., Ltd.)) and was stirred at 200° C. and 300 rpm until the gold wires were completely dissolved.

Table 11 shows the salt concentration in the solution and the time taken for dissolution. The higher the salt concentration, the shorter the time it took to dissolve the gold wires. When the salt concentration was 0.1 mass %, the gold wires did not completely dissolve even after 48 hours.

TABLE 11

| Salt concentration (mass %) | Salt/metal ratio | Dissolution time (h) |
|---|---|---|
| 0.1 | 5 | >48 |
| 0.5 | 25 | 3.5 |
| 1 | 50 | 3.0 |
| 2 | 100 | 2.5 |
| 4 | 200 | 2.5 |
| 6 | 300 | 2.0 |
| 8 | 400 | 1.0 |

TABLE 11-continued

| Salt concentration (mass %) | Salt/metal ratio | Dissolution time (h) |
|---|---|---|
| 10 | 500 | 0.8 |
| 20 | 1000 | 0.7 |

For the case where the salt concentration was 10 mass %, the blue-green alga was immersed in the obtained metal solution in the same manner as in Test Example 14, and the residual ratio of the blue-green alga was determined. The residual ratio was about 79%, which was no different from the case where the salt concentration was 3.8%. From this result, it was found that the salt concentration in the solution affects the dissolution of gold, but does not affect the dissolution of the blue-green alga.

<Test Example 16> Adsorption of Different Metals

Figure 15:
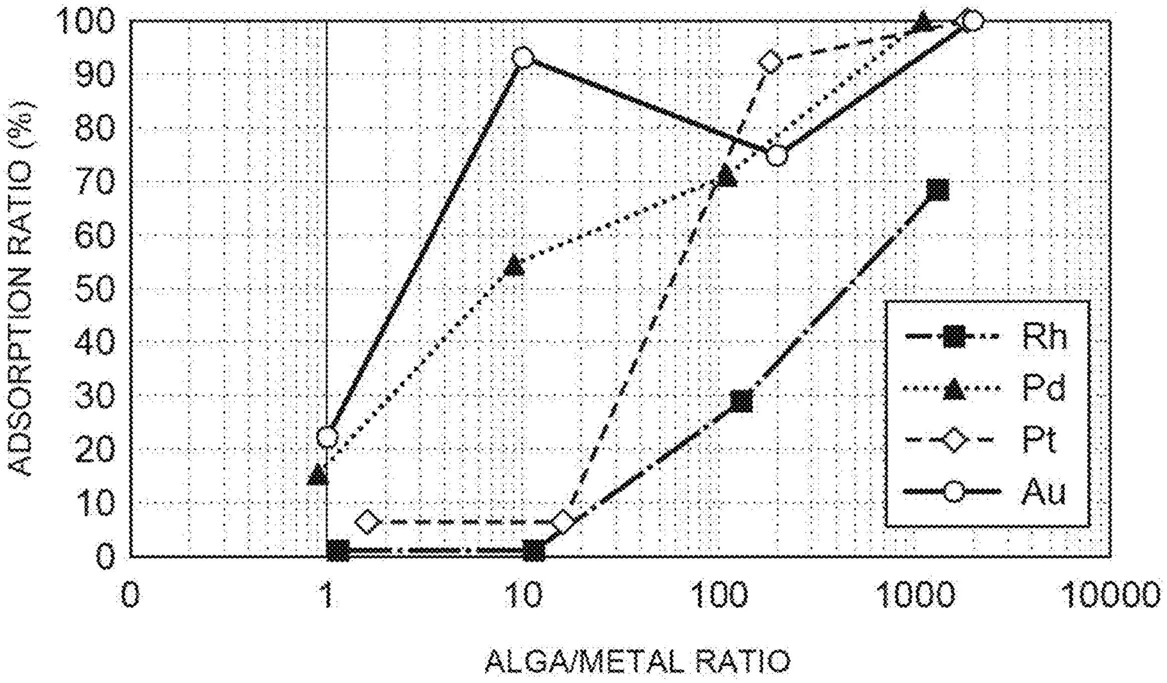
FIG. 15 shows the relationship between the ratio of the mass of a blue-green alga to the mass of rhodium, palladium, platinum, or gold and the ratio of each metal adsorbed to the blue-green alga.

A dry blue-green alga powder was added to 200 mL of deionized water in which rhodium chloride, sodium tetrachloropalladate, hexachloroplatinic acid, and tetrachloroauric acid were dissolved, and the blue-green alga was immersed at room temperature for 3 hours while stirring the obtained metal solution. Table 12 shows the amount of the immersed blue-green alga, the concentrations of metal elements in the metal solution (before immersion), and the ratio of the mass of the blue-green alga to the mass of each metal. The solution containing the blue-green alga was filtered, and the ratio of each metal adsorbed to the blue-green alga was calculated from the concentration of each metal in the filtrate. The adsorption ratios are shown in Table 12 and FIG. 15.

TABLE 12

| | Solution 1 | Solution 2 | Solution 3 | Solution 4 |
|---|---|---|---|---|
| Amount of blue-green alga (g) | 0.02 | 0.2 | 0.1 | 1 |
| Rh concentration (ppm) | 87 | 87 | 3.8 | 3.8 |
| Pd concentration (ppm) | 110 | 110 | 4.5 | 4.5 |
| Pt concentration (ppm) | 62 | 62 | 2.7 | 2.7 |
| Au concentration (ppm) | 99 | 99 | 2.5 | 2.5 |
| Alga/Rh ratio | 1 | 11 | 132 | 1316 |
| Alga/Pd ratio | 1 | 9 | 111 | 1111 |
| Alga/Pt ratio | 2 | 16 | 185 | 1852 |
| Alga/Au ratio | 1 | 10 | 200 | 2000 |
| Rh Adsorption ratio (%) | 1.1 | 1.1 | 28.9 | 68.4 |
| Pd Adsorption ratio (%) | 15.5 | 54.5 | 71.1 | 100.0 |
| Pt Adsorption ratio (%) | 6.5 | 6.5 | 92.2 | 100.0 |
| Au Adsorption ratio (%) | 22.2 | 93.0 | 74.8 | 100.0 |

All of the metals, rhodium, palladium, platinum, and gold, were able to be adsorbed to the blue-green alga. Regarding rhodium and platinum, when the ratio of the mass of blue-green alga to the mass of rhodium and platinum in the metal solution was about 1 to 11 and 1 to 16, respectively, these metals were hardly adsorbed to the blue-green alga. This indicates that, when the alga/Rh ratio is 11 or less and the alga/Pt ratio is 16 or less in a solution containing ions or complex ions of rhodium, palladium, platinum, and gold, gold and palladium can be selectively recovered.

<Test Example 17> Recovery of Metals Using Blue-Green Alga Extract Solution

A dry blue-green alga powder and ethanol were mixed at a ratio of 500 mL of ethanol per 1 g of the dry blue-green alga powder, and were stirred for 1 day. The blue-green alga was removed by filtering the obtained solution to obtain a blue-green alga extract solution. 50 mL of the blue-green alga extract solution was added to 200 mL of deionized water in which 1 ppm, 10 ppm, or 100 ppm of each of rhodium chloride, sodium tetrachloropalladate, hexachloroplatinic acid, and tetrachloroauric acid were dissolved, and the obtained metal solution was stirred at room temperature for 3 hours. The produced metals were recovered by filtering the metal solution, and the recovery ratio of each metal was determined from the concentration of each metal in the filtrate as follows.

$$\text{recovery ratio (\%)} = \{(\text{concentration of metal element in the metal solution before adding a blue-green alga extract solution}) - (\text{concentration of metal element in the filtrate})\} / (\text{concentration of metal element in the metal solution before adding a blue-green alga extract solution}) \times 100$$

Figure 16:
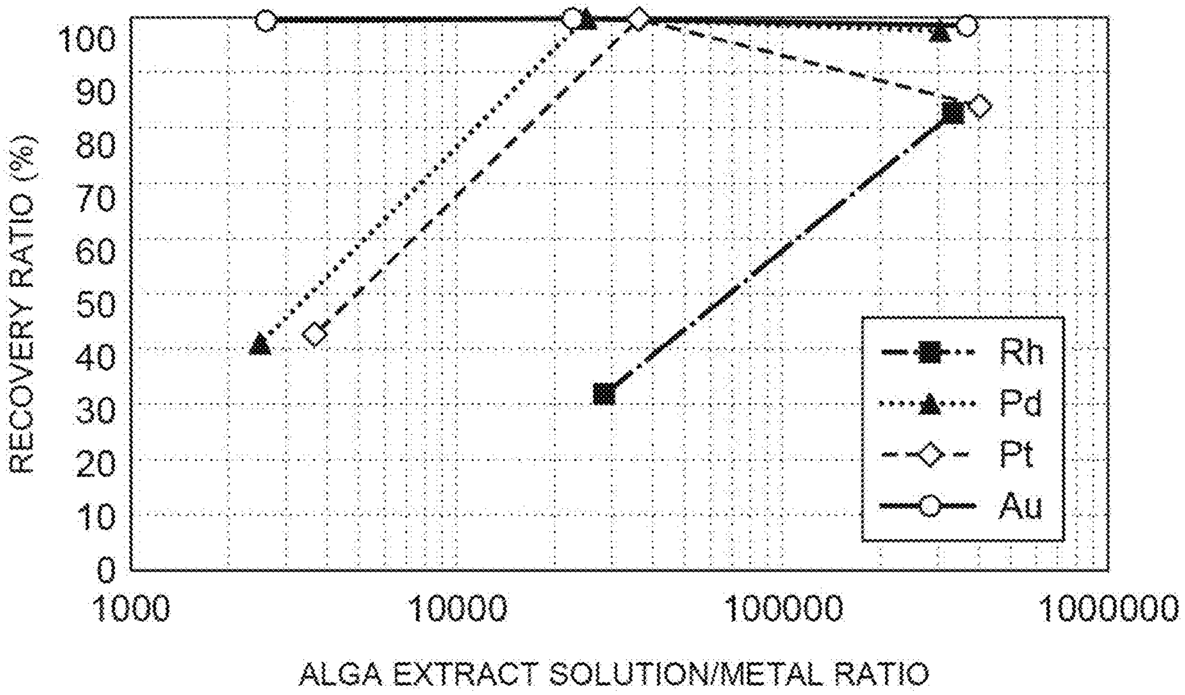
FIG. 16 shows the relationship between the ratio of the mass of a blue-green alga extract solution to the mass of rhodium, palladium, platinum, or gold and the recovery ratio of the respective metals.

The recovery ratios are shown in Table 13 and FIG. 16.

TABLE 13

| | Solution 5 | Solution 6 | Solution 7 |
|---|---|---|---|
| Alga extract solution/Rh ratio | 2809 | 28409 | 333333 |
| Alga extract solution/Pd ratio | 2500 | 25000 | 304878 |
| Alga extract solution/Pt ratio | 3676 | 36232 | 403226 |
| Alga extract solution/Au ratio | 2604 | 22727 | 367647 |
| Rh recovery ratio (%) | — | 31.8 | 82.7 |
| Pd recovery ratio (%) | 41.0 | 99.9 | 97.6 |
| Pt recovery ratio (%) | 42.6 | 99.7 | 83.9 |
| Au recovery ratio (%) | 99.4 | 99.8 | 98.5 |

All of the metals, rhodium, palladium, platinum, and gold, were able to be recovered by the blue-green alga extract solution. In regard to gold, the recovery ratio was high regardless of the blue-green alga extract solution/Au ratio.

<Test Example 18> Examination of Gold Dissolution Conditions 3

0.20 g of a dry blue-green alga powder was added to 200 mL of 1 to 10 mass % of aqua regia in which tetrachloroauric acid-tetrahydrate was dissolved (gold concentration: 10 ppm), and the blue-green alga was immersed at 25° C. for 1 day while stirring the aqueous tetrachloroauric acid solution (alga/Au ratio: 100). The solution containing the blue-green alga was filtered, and the ratio of gold adsorbed to the blue-green alga was calculated from the gold concentration in the filtrate. In addition, after drying the recovered blue-green alga, the mass of the dried blue-green alga was measured and the residual ratio of the blue-green alga was calculated in the same manner as in Test Example 14. The results are shown in Table 14.

TABLE 14

| | pH | Hydrochloric acid concentration (mass %) | Nitric acid concentration (mass %) | Residual ratio of blue-green alga (%) | Adsorption ratio (%) |
|---|---|---|---|---|---|
| 10% aqua regia | 1.7 | 2.6 | 1.5 | 58.1 | 6.0 |

TABLE 14-continued

| | pH | Hydrochloric acid concentration (mass %) | Nitric acid concentration (mass %) | Residual ratio of blue-green alga (%) | Adsorption ratio (%) |
|---|---|---|---|---|---|
| 5% aqua regia | 2.0 | 1.3 | 0.75 | 63.1 | 21.8 |
| 2% aqua regia | 2.3 | 0.53 | 0.30 | 65.1 | 60.0 |
| 1% aqua regia | 2.7 | 0.26 | 0.15 | 54.6 | 86.7 |

The lower the concentration of aqua regia in which the blue-green alga was immersed, the more the gold adsorption ratio improved, and when the concentration of aqua regia was 2 mass % or less (that is, the hydrochloric acid concentration was 0.53 mass % or less and the nitric acid concentration was 0.30 mass % or less), 60% or more of gold was able to be adsorbed to the blue-green alga.

[Supplementary Note]

The present disclosure includes the following aspects.

[1] A metal recovery material comprising a blue-green alga of a genus *Leptolyngbya.*

[2] The metal recovery material according to [1], wherein the blue-green alga of the genus *Leptolyngbya* is a blue-green alga of the genus *Leptolyngbya* deposited with accession number FERM BP-22385 (original deposit date: Jan. 17, 2020, depositary authority: The National Institute of Technology and Evaluation, International Patent Organism Depositary (IPOD) (#120, 2-5-8 Kazusakamatari, Kisarazu-shi, Chiba 292-0818, Japan)).

[3] The metal recovery material according to [1] or [2], wherein the blue-green alga of the genus *Leptolyngbya* is a dried product of the blue-green alga of the genus *Leptolyngbya.*

[4] A method for recovering a metal from a solution comprising a metal ion or metal complex ion, comprising a step of immersing a blue-green alga in a solution comprising a metal ion or metal complex ion to produce a metal, wherein the blue-green alga is a blue-green alga of a genus *Leptolyngbya.*

[5] The method according to [4], wherein the blue-green alga is a blue-green alga of the genus *Leptolyngbya* deposited with accession number FERM BP-22385 (original deposit date: Jan. 17, 2020, depositary authority: The National Institute of Technology and Evaluation, International Patent Organism Depositary (IPOD) (#120, 2-5-8 Kazusakamatari, Kisarazu-shi, Chiba 292-0818, Japan)).

[6] The method according to [4] or [5], wherein the blue-green alga is a blue-green alga treated with an acid.

[7] The method according to [6], wherein the blue-green alga is a blue-green alga further treated with an organic solvent.

[8] The method according to any one of [4] to [7], wherein the solution comprising a metal ion or metal complex ion is a solution comprising an ion or complex ion of at least one metal selected from the group consisting of gold, palladium, platinum, and rhodium, and wherein the metal to be recovered is at least one selected from the group consisting of gold, palladium, platinum, and rhodium.

[9] The method according to any one of [4] to [8], wherein the step of immersing a blue-green alga in the solution comprising a metal ion or metal complex ion is performed at 50° C. or higher.

[10] The method according to any one of [4] to [9], wherein, in the step of immersing a blue-green alga in the solution comprising a metal ion or metal complex ion, the blue-green alga is immersed while irradiating the solution comprising a metal ion or metal complex ion with a visible light or ultraviolet light.

[11] The method according to any one of [4] to [10], wherein, in the step of immersing a blue-green alga in the solution comprising a metal ion or metal complex ion, the blue-green alga is immersed while blocking the solution comprising a metal ion or metal complex ion from light.

[12] The method according to any one of [4] to [11], further comprising a step of recovering the metal.

[13] The method according to [12], wherein the step of recovering the metal comprises a step of filtering the solution in which the blue-green alga has been immersed.

[14] The method according to or [13], wherein the step of recovering the metal comprises a step of ultrasonicating the blue-green alga.

[15] The method according to or [13], wherein the step of recovering the metal comprises a step of firing the blue-green alga.

[16] The method according to any one of [4] to [15], wherein the solution comprising a metal ion or metal complex ion is a solution obtained by bringing a metal element-containing substance into contact with a dissolving solution comprising nitric acid and a salt to dissolve the metal element-containing substance.

[17] The method according to any one of [4] to [15], wherein the solution comprising a metal ion or metal complex ion is a solution obtained by a method comprising steps of:

bringing a metal element-containing substance into contact with a dissolving solution comprising 10 mass % or more of aqua regia to obtain a solution of the metal element-containing substance, and diluting the solution of the metal element-containing substance such that a concentration of aqua regia becomes 5 mass % or less to obtain the solution comprising a metal ion or metal complex ion.

[18] The method according to any one of [4] to [11], wherein the step of immersing a blue-green alga in the solution comprising a metal ion or metal complex ion is a step of (i) immersing the blue-green alga in the solution comprising a metal ion or metal complex ion to produce the metal and to adsorb the metal onto the blue-green alga, and the method further comprises steps of:

(ii) recovering the blue-green alga to which the metal has been adsorbed; and (iii) recovering the metal from the recovered blue-green alga, wherein the step (i) of immersing the blue-green alga in the solution comprising a metal ion or metal complex ion and the step (ii) of recovering the blue-green alga to which the metal has been adsorbed are performed twice or more, and the blue-green algae used for a second and subsequent immersions are blue-green algae different from the blue-green alga recovered from the solution comprising a metal ion or metal complex ion.

[19] A method for producing gold nanoparticles, comprising a step of immersing a blue-green alga in a solution comprising a gold ion or gold complex ion to produce gold nanoparticles, wherein the blue-green alga is a blue-green alga of the genus *Leptolyngbya.*

[20] A method for producing a metal molded product, comprising steps of:

immersing a blue-green alga in a solution comprising a metal ion or metal complex ion to produce a metal and to adsorb the metal onto the blue-green alga;

recovering the blue-green alga to which the metal has been adsorbed;

molding the recovered blue-green alga; and firing the molded blue-green alga to obtain a metal molded product, wherein the blue-green alga is a blue-green alga of the genus *Leptolyngbya.*

[21] The method according to [20], wherein the metal molded product is for personal ornaments.

[22] A method for recovering a metal from a solution comprising a metal ion or metal complex ion, comprising a step of bringing a blue-green alga extract solution into contact with a solution comprising a metal ion or metal complex ion to produce a metal, wherein the blue-green alga is a blue-green alga of the genus *Leptolyngbya.*

The invention claimed is:

1. A metal recovery material comprising a blue-green alga of a genus *Leptolyngbya.*

2. The metal recovery material according to claim 1, wherein the blue-green alga of the genus *Leptolyngbya* is a blue-green alga of the genus *Leptolyngbya* deposited with accession number FERM BP-22385.

3. The metal recovery material according to claim 1, wherein the blue-green alga of the genus *Leptolyngbya* is a dried product of the blue-green alga of the genus *Leptolyngbya.*

4. A method for recovering a metal from a solution comprising a metal ion or metal complex ion, comprising a step of immersing a blue-green alga in a solution comprising a metal ion or metal complex ion to produce a metal, wherein the blue-green alga is a blue-green alga of a genus *Leptolyngbya.*

5. The method according to claim 4, wherein the blue-green alga is a blue-green alga of the genus *Leptolyngbya* deposited with accession number FERM BP-22385.

6. The method according to claim 4, wherein the blue-green alga is a blue-green alga treated with an acid.

7. The method according to claim 6, wherein the blue-green alga is a blue-green alga further treated with an organic solvent.

8. The method according to claim 4, wherein the solution comprising a metal ion or metal complex ion is a solution comprising an ion or complex ion of at least one metal selected from the group consisting of gold, palladium, platinum, and rhodium, and wherein the metal to be recovered is at least one selected from the group consisting of gold, palladium, platinum, and rhodium.

9. The method according to claim 4, wherein the step of immersing a blue-green alga in the solution comprising a metal ion or metal complex ion is performed at 50° C. or higher.

10. The method according to claim 4, wherein, in the step of immersing a blue-green alga in the solution comprising a metal ion or metal complex ion, the blue-green alga is immersed while irradiating the solution comprising a metal ion or metal complex ion with a visible light or ultraviolet light.

11. The method according to claim 4, wherein, in the step of immersing a blue-green alga in the solution comprising a metal ion or metal complex ion, the blue-green alga is immersed while blocking the solution comprising a metal ion or metal complex ion from light.

12. The method according to claim 4, further comprising a step of recovering the metal, wherein the step of recovering the metal comprises a step of filtering the solution in which the blue-green alga has been immersed.

13. The method according to claim 4, further comprising a step of recovering the metal, wherein the step of recovering the metal comprises a step of ultrasonicating the blue-green alga.

14. The method according to claim 4, further comprising a step of recovering the metal, wherein the step of recovering the metal comprises a step of firing the blue-green alga.

15. The method according to claim 4, wherein the solution comprising a metal ion or metal complex ion is a solution obtained by bringing a metal element-containing substance into contact with a dissolving solution comprising nitric acid and a salt to dissolve the metal element-containing substance.

16. The method according to claim 4, wherein the solution comprising a metal ion or metal complex ion is a solution obtained by a method comprising steps of:

bringing a metal element-containing substance into contact with a dissolving solution comprising 10 mass % or more of aqua regia to obtain a solution of the metal element-containing substance, and diluting the solution of the metal element-containing substance such that a concentration of aqua regia becomes 5 mass % or less to obtain the solution comprising a metal ion or metal complex ion.

17. The method according to claim 4, wherein the step of immersing a blue-green alga in the solution comprising a metal ion or metal complex ion is a step of (i) immersing the blue-green alga in the solution comprising a metal ion or metal complex ion to produce the metal and to adsorb the metal onto the blue-green alga, and the method further comprises steps of:

(ii) recovering the blue-green alga to which the metal has been adsorbed; and (iii) recovering the metal from the recovered blue-green alga, wherein the step (i) of immersing the blue-green alga in the solution comprising a metal ion or metal complex ion and the step (ii) of recovering the blue-green alga to which the metal has been adsorbed are performed twice or more, and the blue-green algae used for a second and subsequent immersions are blue-green algae different from the blue-green alga recovered from the solution comprising a metal ion or metal complex ion.

18. A method for producing gold nanoparticles, comprising a step of immersing a blue-green alga in a solution comprising a gold ion or gold complex ion to produce gold nanoparticles, wherein the blue-green alga is a blue-green alga of a genus *Leptolyngbya.*

19. A method for recovering a metal from a solution comprising a metal ion or metal complex ion, comprising a step of bringing a blue-green alga extract solution into contact with a solution comprising a metal ion or metal complex ion to produce a metal, wherein the blue-green alga is a blue-green alga of a genus *Leptolyngbya*.

* * * * *